(12) United States Patent
Sikora

(10) Patent No.: US 12,098,424 B2
(45) Date of Patent: Sep. 24, 2024

(54) CONTROL NUCLEIC ACID SEQUENCES FOR USE IN SEQUENCING-BY-SYNTHESIS AND METHODS FOR DESIGNING THE SAME

(71) Applicant: LIFE TECHNOLOGIES CORPORATION, Carlsbad, CA (US)

(72) Inventor: Marcin Sikora, Burlingame, CA (US)

(73) Assignee: Life Technologies Corporation, Carlsbad, CA (US)

( * ) Notice: Subject to any disclaimer, the term of this patent is extended or adjusted under 35 U.S.C. 154(b) by 495 days.

(21) Appl. No.: 16/999,001

(22) Filed: Aug. 20, 2020

(65) Prior Publication Data

US 2021/0102249 A1 Apr. 8, 2021

Related U.S. Application Data

(62) Division of application No. 15/923,633, filed on Mar. 16, 2018, now Pat. No. 10,760,125, which is a division of application No. 14/338,682, filed on Jul. 23, 2014, now Pat. No. 9,926,597.

(60) Provisional application No. 61/858,828, filed on Jul. 26, 2013.

(51) Int. Cl.
*C12Q 1/6874* (2018.01)
*G16B 30/00* (2019.01)
*G16B 30/10* (2019.01)

(52) U.S. Cl.
CPC .......... *C12Q 1/6874* (2013.01); *G16B 30/00* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,750,341 A | 5/1998 | Macevicz | |
| 5,854,033 A | 12/1998 | Lizardi | |
| 6,172,214 B1 | 1/2001 | Brenner et al. | |
| 6,174,670 B1 | 1/2001 | Wittwer et al. | |
| 6,210,891 B1 | 4/2001 | Nyren et al. | |
| 6,235,475 B1 | 5/2001 | Brenner et al. | |
| 6,258,568 B1 | 7/2001 | Nyren | |
| 6,274,320 B1 | 8/2001 | Rothberg et al. | |
| 6,404,907 B1 | 6/2002 | Gilchrist et al. | |
| 6,828,100 B1 | 12/2004 | Ronaghi | |
| 6,833,246 B2 | 12/2004 | Balasubramanian | |
| 6,911,327 B2 | 6/2005 | Mcmillan et al. | |
| 7,037,687 B2 | 5/2006 | Williams et al. | |
| 7,117,095 B2 | 10/2006 | Hubbell et al. | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 9,926,597 B2 | 3/2018 | Sikora et al. | |
| 2003/0119014 A1* | 6/2003 | Donner et al. | C12Q 1/6874 435/6.12 |
| 2004/0018506 A1 | 1/2004 | Koehler et al. | |
| 2004/0197793 A1 | 10/2004 | Hassibi et al. | |
| 2004/0197845 A1 | 10/2004 | Hassibi et al. | |
| 2005/0084851 A1 | 4/2005 | Ronaghi et al. | |
| 2006/0147935 A1 | 7/2006 | Linnarsson | |
| 2007/0092872 A1 | 4/2007 | Rothberg et al. | |
| 2007/0207471 A1 | 9/2007 | Osaka et al. | |
| 2007/0219367 A1 | 9/2007 | Shchepinov et al. | |
| 2007/0281300 A1 | 12/2007 | Russell et al. | |

(Continued)

FOREIGN PATENT DOCUMENTS

| | | | | |
|---|---|---|---|---|
| EP | 1260592 A1 * | 11/2002 | ........... | C12Q 1/6837 |
| WO | WO-2010138182 A2 | 12/2010 | | |

(Continued)

OTHER PUBLICATIONS

Ashlock et al., "DNA error correcting codes: No crossover," IEEE Symposium on Computational Intelligence in Bioinformatics and Computational Biology, 38-45 (2009).
Brenner, S. et al. "Encoded Combinatorial Chemistry". Proc. Natl. Acad. Sci. USA 89, 5381-5383 (1992).
Faircloth et al., "Large sets of edit-metric sequence identification tags to facilitate large-scale multiplexing of reads from massively parallel sequencing," Nature Proc., 1-15 (2011).
Fu, et al. Counting individual DNA molecules by the stochastic attachment of diverse labels. Proc Natl Acad Sci U S A. May 31, 2011;108(22):9026-31. Epub May 11, 2011.
Gilles et al., "Accuracy and Quality Assessment of 454 GS-FLX Titanium Prosequencing", BMC Genomics, vol. 12, No. 245, 2011, 11 pages.

(Continued)

*Primary Examiner* — Kaijiang Zhang

(57) ABSTRACT

A method for designing test or control sequences may include identifying, using a variant caller, loci with systematic errors present in a plurality of sequencing runs included in a training set of sequencing runs obtained using sequencing-by-synthesis; and selecting a representative set of loci, including selecting from the identified loci an approximately equal number of loci involving errors in A, T, C, and G homopolymers and selecting from the identified loci an approximately equal number of loci involving homopolymers having a length of two, three, and four.

14 Claims, 9 Drawing Sheets

Specification includes a Sequence Listing.

(56) References Cited

U.S. PATENT DOCUMENTS

| | | |
|---|---|---|
| 2008/0166727 A1 | 7/2008 | Esfandyarpour et al. |
| 2008/0182757 A1 | 7/2008 | Heiner et al. |
| 2008/0286762 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0137404 A1 | 5/2009 | Drmanac et al. |
| 2009/0176200 A1 | 7/2009 | Wakita et al. |
| 2009/0312188 A1 | 12/2009 | Duer et al. |
| 2010/0035252 A1 | 2/2010 | Rothberg et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0160078 A1 | 6/2011 | Fodor et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0264621 A1 | 10/2012 | Hubbell et al. |
| 2012/0301926 A1 | 11/2012 | Chen et al. |
| 2013/0060482 A1 | 3/2013 | Sikora et al. |
| 2014/0296080 A1 | 10/2014 | Hubbell et al. |
| 2014/0316716 A1 | 10/2014 | Jiang et al. |

FOREIGN PATENT DOCUMENTS

| | | |
|---|---|---|
| WO | WO-2012044847 A1 | 4/2012 |
| WO | WO-2012129363 A2 | 9/2012 |

OTHER PUBLICATIONS

Golay, M., "Notes on Digital Coding," Proc. IRE, 37(6):657 (1949).
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hamming, R.W., "Error Detecting and Error Correcting Codes," Bell Syst. Tech. J., 29(2):147-160 (1950) (http://www.alcatel-lucent.com/bstj/vol. 29-1950/articles/bstj29-2-147.pdf).
Kanemasu, M., "Golay Codes," MIT Undergraduate Journal of Mathematics, 1 :95-99 (1999) (available at http://www-math.mit.edu/phase2/UJM/voi1/MKANEM-1.PDF).
Krishnan et al., "Barcodes for DNA sequencing with guaranteed error correction capability," Electron. Lett., 47(4):1-2 (2011).
Lee, "Some Properties of Nonbinary Error-Correcting Codes," IRE Transactions on Information TheoJ:Y., 77-82 (1958).
Loman N J., et al., "Performance comparison of benchtop high-throughput sequencing platforms," Nature Biotechnology, vol. 30, No. 5, May 2012, pp. 434-439.
Margulies et al., "Genome Sequencing in Microfabricated High-Density Picolitre Reactors", Nature, vol. 437, No. 15, 2005, pp. 376-380.
Margulies et al., "Supplemental Materials, Genome Sequencing in Microfabricated High-Density Picolitre Reactors", Nature, vol. 437, No. 15, 2005, pp. 1-34.
Pavel Skums et al: "Efficient error correction for next-generation sequencing of viral amplicons" BMC Bioinformatics. Biomed Central. London. GB. vol 13. No. Suppl 10. Jun. 25, 2012 (Jun. 25, 2012). p. 56. XP021094804. ISSN: 1471-2105. DOI: 10.1186/1471-2105-13-S10-S6.
Pourmand et al., "Direct electrical detection of DNA synthesis", Proceedings of the National Academy of Sciences, vol. 103, No. 17, Apr. 2006, pp. 6466-6470.
Pourmand et al., "Multiplex Pyrosequencing," Nucleic Acids Res., 30(7)(e31):1-5 (2002).
Qiu et al., "DNA Sequence-Based 'Bar Codes' for Tracking the Origins of Expressed Sequence Tags from a Maize eDNA Library Constructed Using Multiple mRNA Sources," Plant Physiol., 133 :475-481 (2003).
Quail et al., "SASI-Seq: sample assurance Spike-Ins, and highly differentiating 384 barcoding for Illumina sequencing," BMC Genomics, 15:110 (2014).
Reid et al., "Proposed methods for testing and selecting the ERCC external RNA controls," BMC Genomics, 6:150 (2005).
Ronaghi et al., "A Sequencing Method Based on Real-Time Pyrophosphate", Science, vol. 281, No. 5375, Jul. 1998, pp. 363-365.
Ronaghi, "Pyrosequencing Sheds Light on DNA Sequencing," Genome Research, 11:3-11 (2001).
Schwartz et al., "The Structure of Single-Track Gray Codes," IEEE Transactions on Information Theory, 45(7):2383-2396 (1999).
Shiroguchi et al., "Digital RNA sequencing minimizes sequence-dependent bias and amplification noise with optimized single-molecule barcodes," Proc. Natl. Adac. Sci. U.S.A, 109(4):1347-1352(2012).
Yan et al., "Yeast Barcoders: a chemogenomic application of a universal donor-strain collection carrying bar-code identifiers," Nature Methods, 5(8):719-725 (2008).

* cited by examiner

CONTROL NUCLEIC ACID SEQUENCES FOR USE IN SEQUENCING-BY-SYNTHESIS AND METHODS FOR DESIGNING THE SAME

CROSS-REFERENCE TO RELATED APPLICATIONS

This application is a divisional of U.S. application Ser. No. 15/923,633, filed Mar. 16, 2018. U.S. application Ser. No. 15/923,633, is a divisional of U.S. application Ser. No. 14/338,682, filed Jul. 23, 2014, which claims the benefit of U.S. Prov. Appl. No. 61/858,828, filed Jul. 26, 2013, each of which is incorporated by reference herein; each in its entirety.

SEQUENCE LISTING

This application contains a Sequence Listing which was submitted electronically in ASCII format in parent U.S. application Ser. No. 15/923,633 and is incorporated by reference herein in its entirety.

FIELD

This application generally relates to control nucleic acid sequences and methods for designing the same, and, more specifically, to control nucleic acid sequences for use in sequencing-by-synthesis and methods for designing the same using a variant caller to identify loci with systematic errors.

BACKGROUND

Control nucleic acid sequences may sometimes be used to facilitate assessment and/or analysis of nucleic acid sequencing data obtained in various ways, including using next-generation sequencing systems such as, for example, the Ion PGM™ and Ion Proton™ systems implementing Ion Torrent™ sequencing technology (see, e.g., U.S. Pat. No. 7,948,015 and U.S. Pat. Appl. Publ. Nos. 2010/0137143, 2009/0026082, and 2010/0282617, which are all incorporated by reference herein in their entirety). For example, certain relatively short (e.g., less than 100 base pairs) nucleic acid sequences constrained to contain homopolymers of only certain lengths (e.g., homopolymers of length two, three, or four; homopolymers of length no more than 2; or homopolymers of length no more than 1) may be used to attempt to assess potential error failure modes that may be related to homopolymer of such lengths and may more generally be indicative of performance. However, these nucleic acid sequences may in some cases be oversensitive and may not be able to properly capture or detect certain error modes of interest. There is a need for new and improved control nucleic acid sequences and methods for designing the same that can better facilitate assessment and/or analysis of nucleic acid sequencing data obtained using the above-mentioned systems or other sequencing systems/platforms.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

SUMMARY

Figure 1:
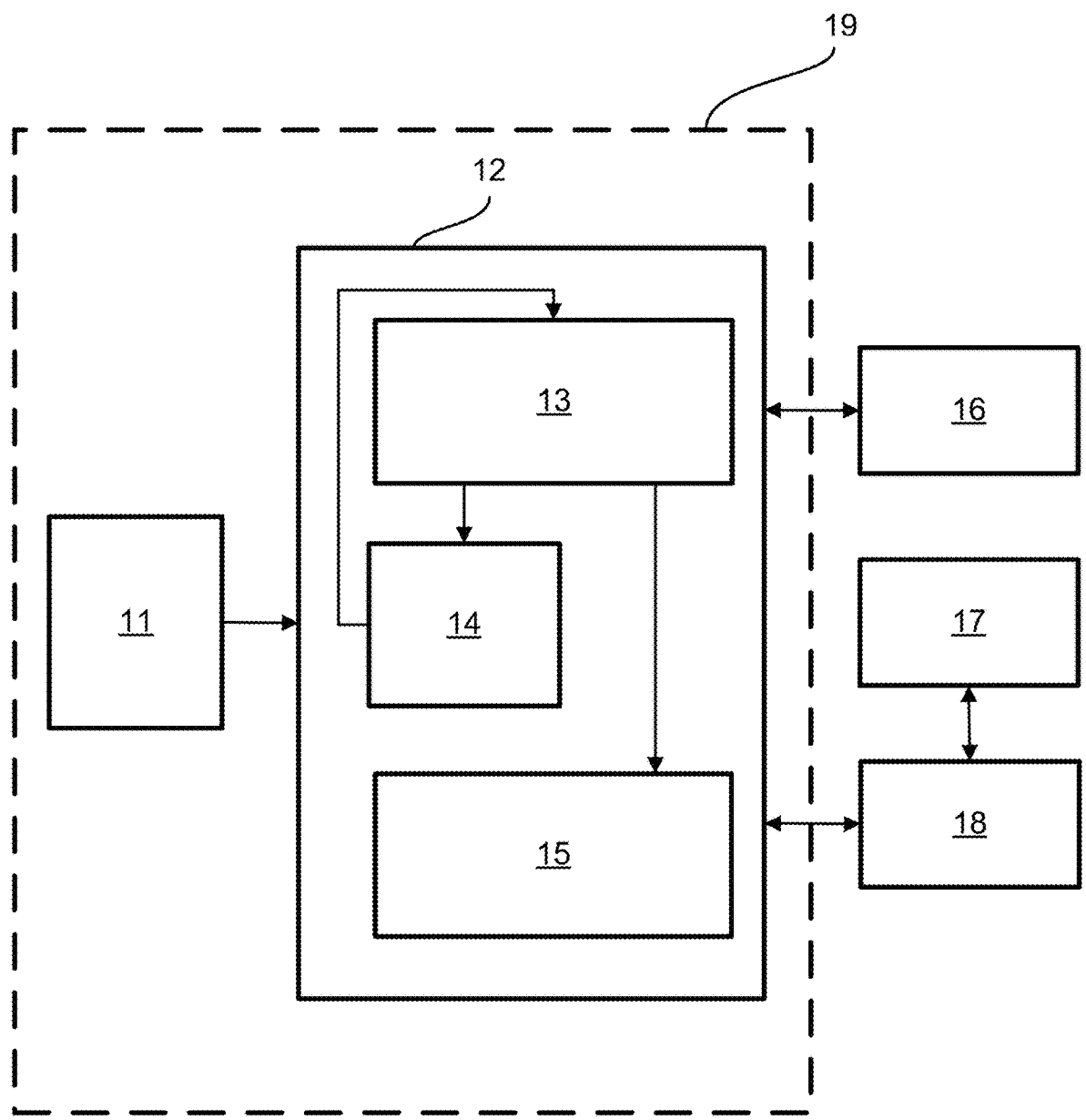
FIG. 1 illustrates an exemplary system for nucleic acid sequencing and/or analysis.

According to an exemplary embodiment, there is provided a method for nucleic acid sequencing, comprising: (a) disposing a plurality of template polynucleotide strands in a plurality of defined spaces disposed on a sensor array, at least some of the template polynucleotide strands comprising a test or control sequence; (b) exposing a plurality of the template polynucleotide strands in the defined spaces to a series of flows of nucleotide species flowed according to a predetermined ordering; and (c) determining sequence information for a plurality of the template polynucleotide strands in the defined spaces based on the flows of nucleotide species to generate a plurality of sequencing reads corresponding to the template polynucleotide strands, wherein the test or control sequence comprises a sequence determined by identifying, using a variant caller, loci with systematic errors present in a plurality of sequencing runs included in a training set of sequencing runs.

According to an exemplary embodiment, there is provided a system, including: a plurality of template polynucleotide strands disposed in a plurality of defined spaces disposed on a sensor array, at least some of the template polynucleotide strands comprising a test or control sequence, wherein the test or control sequence comprises a sequence determined by identifying, using a variant caller, loci with systematic errors present in a plurality of sequencing runs included in a training set of sequencing runs; a machine-readable memory; and a processor configured to execute machine-readable instructions, which, when executed by the processor, cause the system to perform a method for nucleic acid sequencing, comprising: (a) exposing a plurality of the template polynucleotide strands in the defined spaces to a series of flows of nucleotide species flowed according to a predetermined ordering; and (b) determining sequence information for a plurality of the template polynucleotide strands in the defined spaces based on the flows of nucleotide species to generate a plurality of sequencing reads corresponding to the template polynucleotide strands.

According to an exemplary embodiment, there is provided a method for designing test or control sequences, comprising: identifying, using a variant caller, loci with systematic errors present in a plurality of sequencing runs included in a training set of sequencing runs obtained using sequencing-by-synthesis; selecting a representative set of loci, including selecting from the identified loci an approximately equal number of loci involving errors in A, T, C, and G homopolymers and selecting from the identified loci an approximately equal number of loci involving homopolymers having a length of two, three, and four.

EXEMPLARY EMBODIMENTS

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

According to various exemplary embodiments, control nucleic acid sequences for test fragments and/or in line controls, and methods for designing the same, are disclosed herein. Such control nucleic acid sequences and methods for designing the same may improve the ability of control nucleic acid sequences to allow identification of compromised sequencing experiments that produce data of substandard quality as a result of sequencing failure modes. Such sequencing failure modes may include sequencing failure modes that lead to reduced accuracy, which may include one or more sequencing failure modes such as: systematic errors for high homopolymers in general, systematic errors for high homopolymers in specific contexts, and/or systematic errors for specific "difficult" sequences not involving high homopolymers. Such control nucleic acid sequences and methods for designing the same may help detect and/or reduce certain systematic errors and improve overall sequencing accuracy (especially in the case of long homopolymers), which may in turn improve downstream processing such as variant calling.

FIG. 1 illustrates an exemplary system for nucleic acid sequencing and/or analysis. The system includes an apparatus or sub-system for nucleic acid sequencing and/or analysis 11, a computing server/node/device 12 including a base calling engine 13, a recalibration engine 14, a post-processing engine 15, and a display 16, which may be internal and/or external. The apparatus or sub-system for nucleic acid sequencing and/or analysis 11 may be any type of instrument that can generate nucleic acid sequence data from nucleic acid samples, which may include a nucleic acid sequencing instrument, a real-time/digital/quantitative PCR instrument, a microarray scanner, etc. The nucleic acid samples may include control/test nucleic acid samples as further described herein and/or library nucleic acid samples. The computing server/node/device 12 may be a workstation, mainframe computer, distributed computing node (part of a "cloud computing" or distributed networking system), personal computer, mobile device, etc. The base calling engine 13 may be any suitable base caller and may be configured to include various signal/data processing modules that may be configured to receive signal/data from the apparatus or sub-system for nucleic acid sequencing and/or analysis 11 and perform various processing steps, such as conversion from flow space to base space, determination of base calls for some or the entirety of a sequencing data set, and determination of base call quality values. In an embodiment, the base calling engine 13 may implement one or more features described in Davey et al., U.S. Pat. Appl. Publ. No. 2012/0109598, published on May 3, 2012, and/or Sikora et al., U.S. Pat. Appl. Publ. No. 2013/0060482, published on Mar. 7, 2013, which are all incorporated by reference herein in their entirety. The base calling engine 13 may also include a mapping or alignment module for mapping or aligning reads to a reference sequence or genome, which may be a whole/partial genome, whole/partial exome, etc. In an embodiment, the mapping or alignment module may include any suitable aligner, including the Torrent Mapping Alignment Program (TMAP), for example. The recalibration engine 14 may be configured to recalibrate base calls or related intensity values or parameters based on an analysis of base calling and alignment performed by the base calling engine 13, which recalibrated base calls or related intensity values or thresholds or parameters may be fed back into the base calling engine 13 for improving the accuracy of base calls. In an embodiment, the recalibration engine 14 may implement one or more features described in Jiang et al., U.S. patent application Ser. No. 14/255,528, filed on Apr. 17, 2014, which is incorporated by reference herein in its entirety. The exemplary system may also include a client device terminal 17, which may include a data analysis API or module and may be communicatively connected to the computing server/node/device 12 via a network connection 18 that may be a "hardwired" physical network connection (e.g., Internet, LAN, WAN, VPN, etc.) or a wireless network connection (e.g., Wi-Fi, WLAN, etc.). The post-processing engine 15 may be configured to include various signal/data processing modules that may be configured to make variant calls and apply post-processing to variant calls, which may include annotating various variant calls and/or features, converting data from flow space to base space, filtering of variants, and formatting the variant data for display or use by client device terminal 17. Variant calls may be made using any suitable variant caller, including the Germ-Line Variant Caller and the Torrent Variant Caller (TVC) Plug-ins for Ion Torrent™ sequencing technology. In an embodiment, the variant caller may implement one or more features described in Hubbell et al., U.S. patent application Ser. No. 14/200, 942, filed Mar. 7, 2014, which is incorporated by reference herein in its entirety. In an embodiment, the apparatus or sub-system for nucleic acid sequencing and/or analysis 11 and the computing server/node/device 12 may be integrated into a single instrument or system comprising components present in a single enclosure 19. The client device terminal 17 may be configured to communicate information to and/or control the operation of the computing server/node/device 12 and its modules and/or operating parameters.

Figure 2:
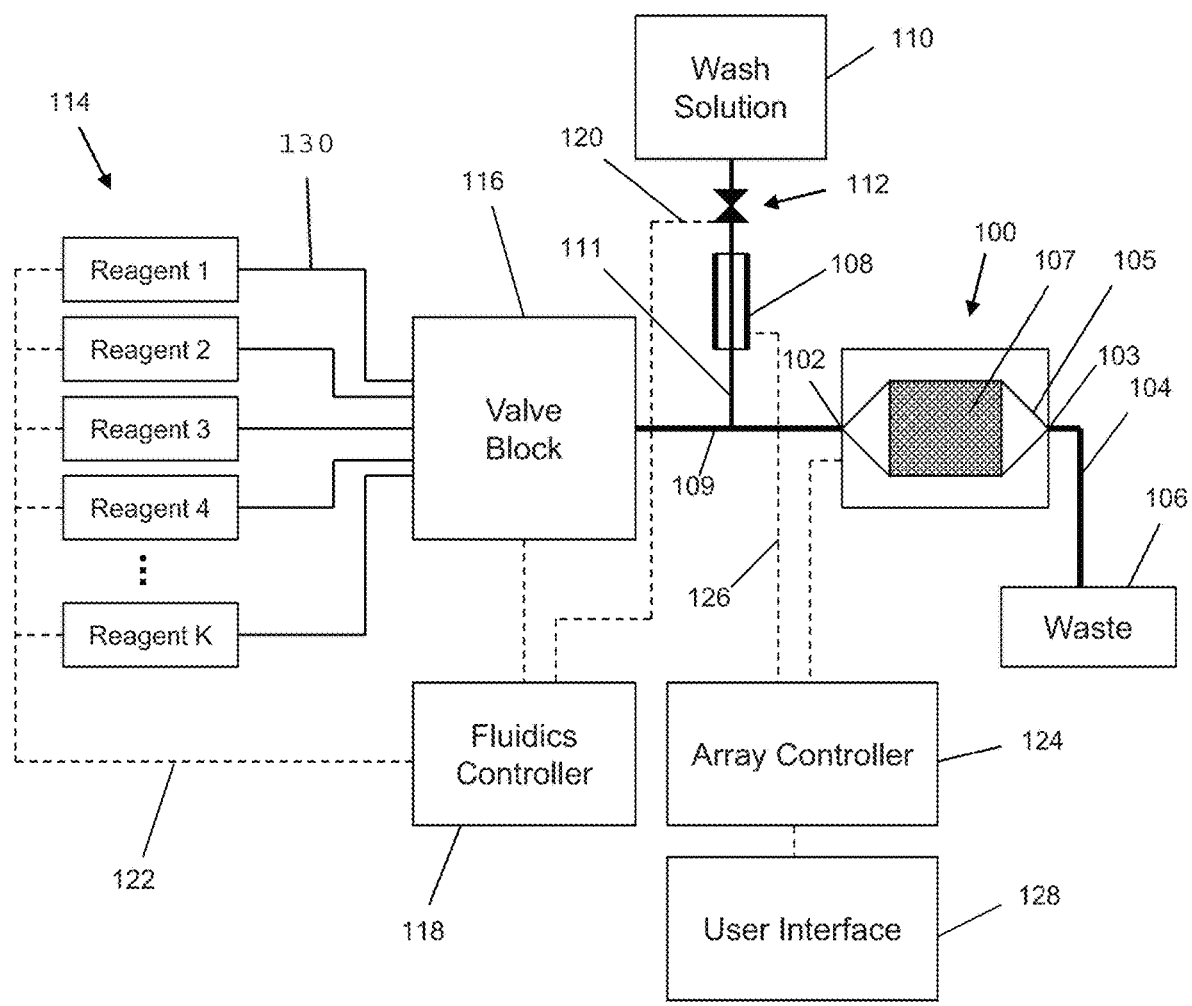
FIG. 2 illustrates exemplary components of an apparatus for nucleic acid sequencing.

FIG. 2 illustrates exemplary components of an apparatus for nucleic acid sequencing. Such an apparatus could be used as apparatus or sub-system for nucleic acid sequencing and/or analysis 11 of FIG. 1. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The reagents 114 may, for example, contain dNTPs to be flowed through passages 130 and through the valve block 116, which may control the flow of the reagents 114 to flow chamber 105 (also referred to herein as a reaction chamber) via passage 109. The system may include a reservoir 110 for containing a wash solution that may be used to wash away dNTPs, for example, that may have previously been flowed. The microwell array 107 may include an array of defined spaces, such as microwells, for example, that is operationally associated with a sensor array so that, for example, each microwell has a sensor suitable for detecting an analyte or reaction property of interest. The defined spaces may include control/test nucleic acid samples as further described herein and/or library nucleic acid samples. The microwell array 107 may preferably be integrated with the sensor array as a single device or chip. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The fluidics controller 118 may be programmed to control driving forces for flowing reagents 114 and the operation of valve 112 and valve block 116 to deliver reagents to the flow cell and sensor array 100 according to a predetermined reagent flow ordering.

In this application, "defined space" generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip, or by isolated hydrophobic areas on a generally hydrophobic surface. Defined spaces may be arranged as an array, which may be a substantially planar one-dimensional or two-dimensional arrangement of elements such as sensors or wells. Defined spaces, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information or signal about a chemical reaction or desired association event, for example, a nucleotide incorporation event and/or a related ion concentration (e.g., a pH measurement). The sensors may include at least one ion sensitive field effect transistor ("ISFET") or chemically sensitive field effect transistor ("chemFET").

Figure 3:
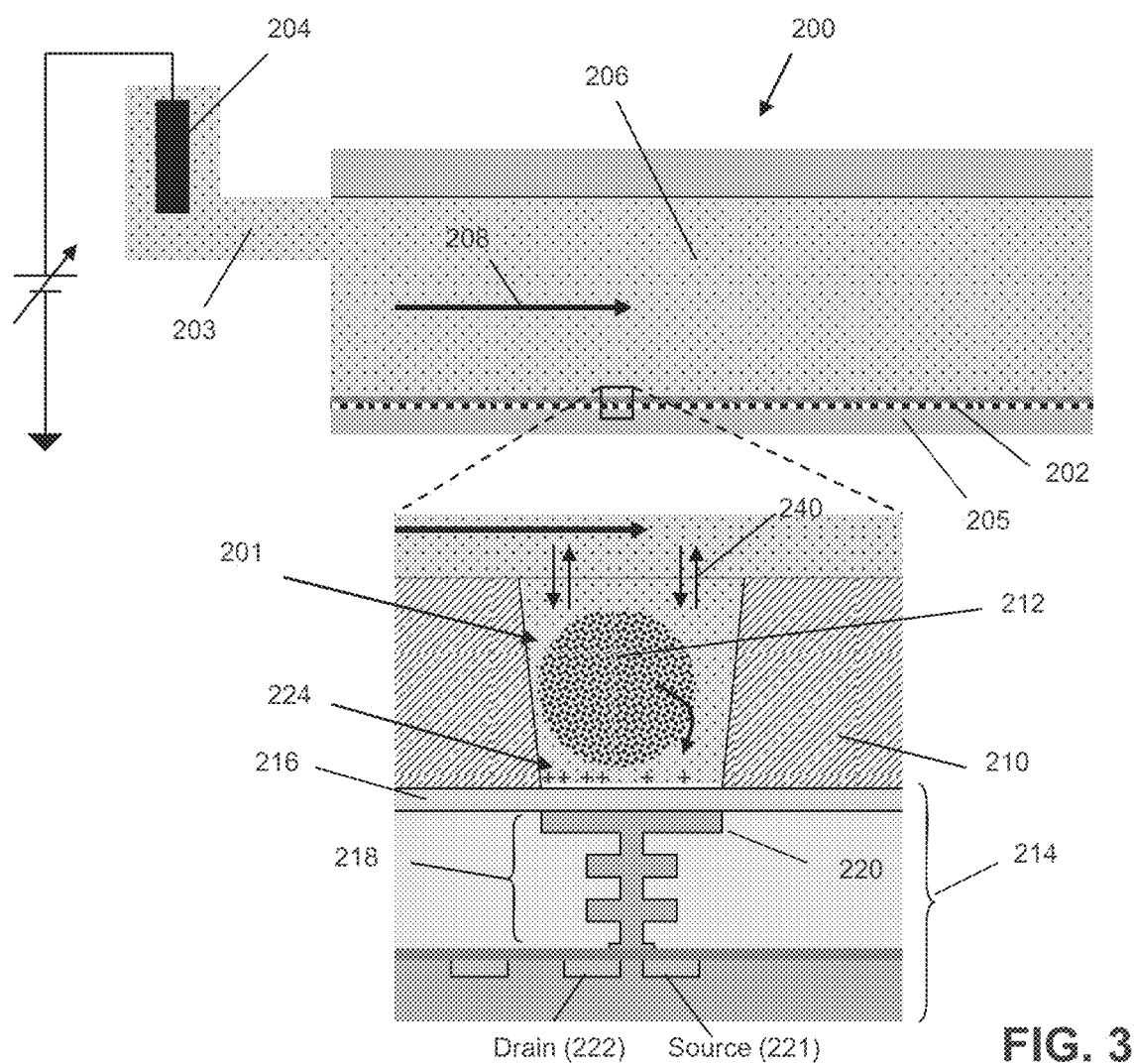
FIG. 3 illustrates an exemplary flow cell for nucleic acid sequencing.

FIG. 3 illustrates an exemplary flow cell for nucleic acid sequencing. The flow cell 200 includes a microwell array 202, a sensor array 205, and a flow chamber 206 in which a reagent flow 208 may move across a surface of the microwell array 202, over open ends of microwells in the microwell array 202. The flow of reagents (e.g., nucleotide species) can be provided in any suitable manner, including delivery by pipettes, or through tubes or passages connected to a flow chamber. A microwell 201 in the microwell array 202 may have any suitable volume, shape, and aspect ratio. A sensor 214 in the sensor array 205 may be an ISFET or a chemFET sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220. In an embodiment, a reference electrode 204 may be fluidly connected to the flow chamber 206 via a flow passage 203. In an embodiment, the microwell array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include one or more copies of a nucleic acid analyte, which may include a control/test nucleic acid sample as further described herein and/or a library nucleic acid sample, obtained using any suitable technique.

Figure 4:
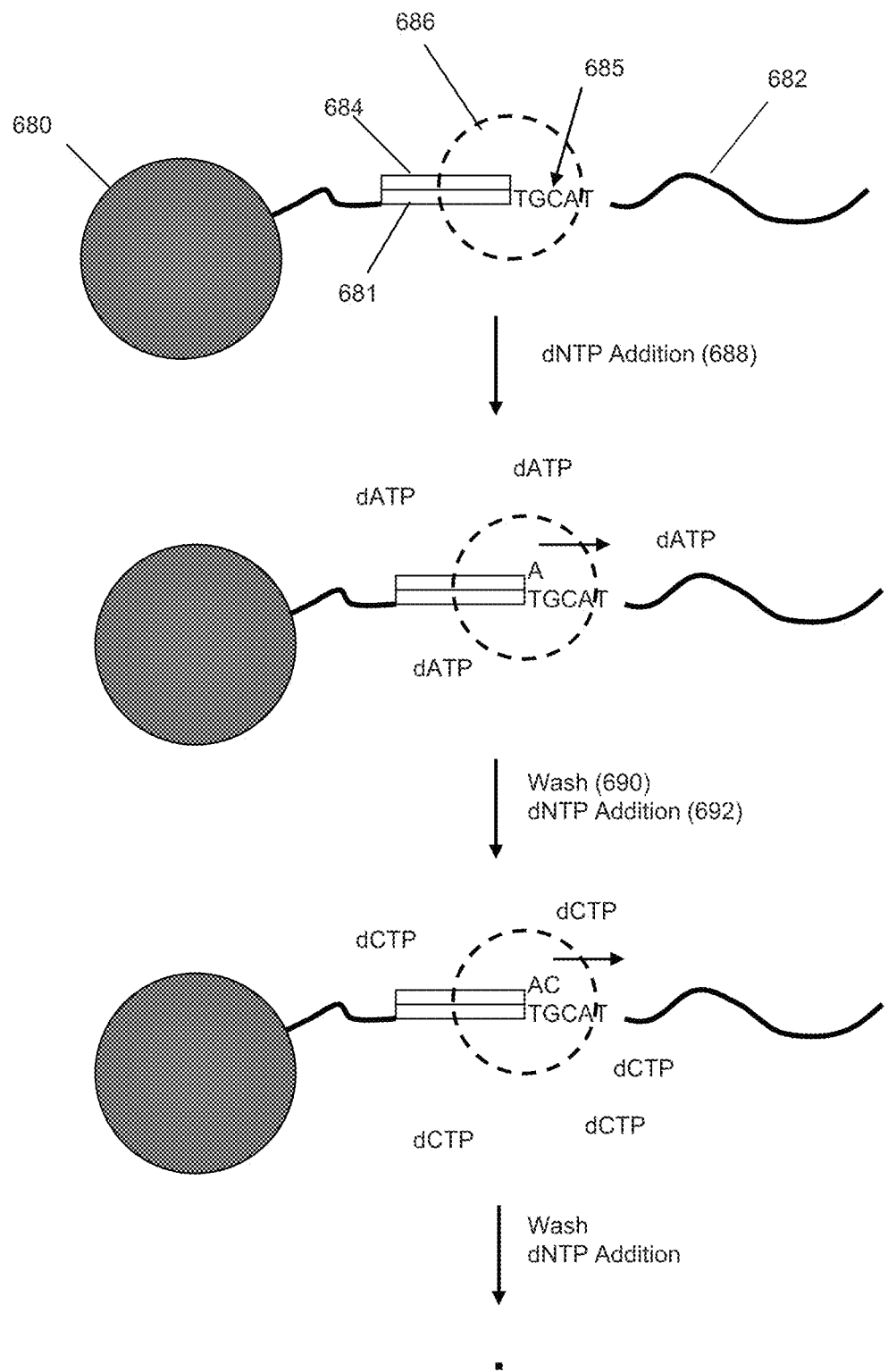
FIG. 4 illustrates an exemplary process for label-free, pH-based sequencing.

FIG. 4 illustrates an exemplary process for label-free, pH-based sequencing. A template 682 with sequence 685 and a primer binding site 681 are attached to a solid phase support 680. The template 682 may comprise a control/test nucleic acid sample as further described herein and/or a library nucleic acid sample. The template 682 may be attached as a clonal population to a solid support, such as a microparticle or bead, for example, and may be prepared as disclosed in Leamon et al., U.S. Pat. No. 7,323,305. In an embodiment, the template may be associated with a substrate surface or present in a liquid phase with or without being coupled to a support. A primer 684 and DNA polymerase 686 are annealed to the template 682 so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed. In step 692, the next dNTP (shown as dCTP) is added, and the DNA polymerase 686 incorporates a nucleotide "C" (since "G" is the next nucleotide in the template 682). More details about pH-based nucleic acid sequencing may be found in U.S. Pat. No. 7,948,015 and U.S. Pat. Appl. Publ. Nos. 2010/0137143, 2009/0026082, and 2010/0282617.

In an embodiment, the primer-template-polymerase complex may be subjected to a series of exposures of different nucleotides in a pre-determined sequence or ordering. If one or more nucleotides are incorporated, then the signal resulting from the incorporation reaction may be detected, and after repeated cycles of nucleotide addition, primer extension, and signal acquisition, the nucleotide sequence of the template strand may be determined. The output signals measured throughout this process depend on the number of nucleotide incorporations. Specifically, in each addition step, the polymerase extends the primer by incorporating added dNTP only if the next base in the template is complementary to the added dNTP. With each incorporation, an hydrogen ion is released, and collectively a population released hydrogen ions change the local pH of the reaction chamber. The production of hydrogen ions may be monotonically related to the number of contiguous complementary bases (e.g., homopolymers) in the template. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP." The predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG ACTG . . . "), may be based in whole or in part on some other pattern of reagent flows (such as, e.g., any of the various reagent flow orderings discussed in Hubbell et al., U.S. Pat. Appl. Publ. No. 2012/0264621, published Oct. 18, 2012, which is incorporated by reference herein in its entirety), and may also be based on some combination thereof.

In various embodiments, output signals due to nucleotide incorporation may be processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal decay (e.g., enzyme efficiency loss) estimations, signal corrections, and model-based signal predictions, and may identify or estimate base calls for each flow for each defined space. Any suitable base calling method may be used, including as described in Davey et al., U.S. Pat. Appl. Publ. No. 2012/0109598, published on May 3, 2012, and/or Sikora et al., U.S. Pat. Appl. Publ. No. 2013/0060482, published on Mar. 7, 2013, which are all incorporated by reference herein in their entirety, recognizing of course that more accurate base callers may yield better results.

Figure 5:
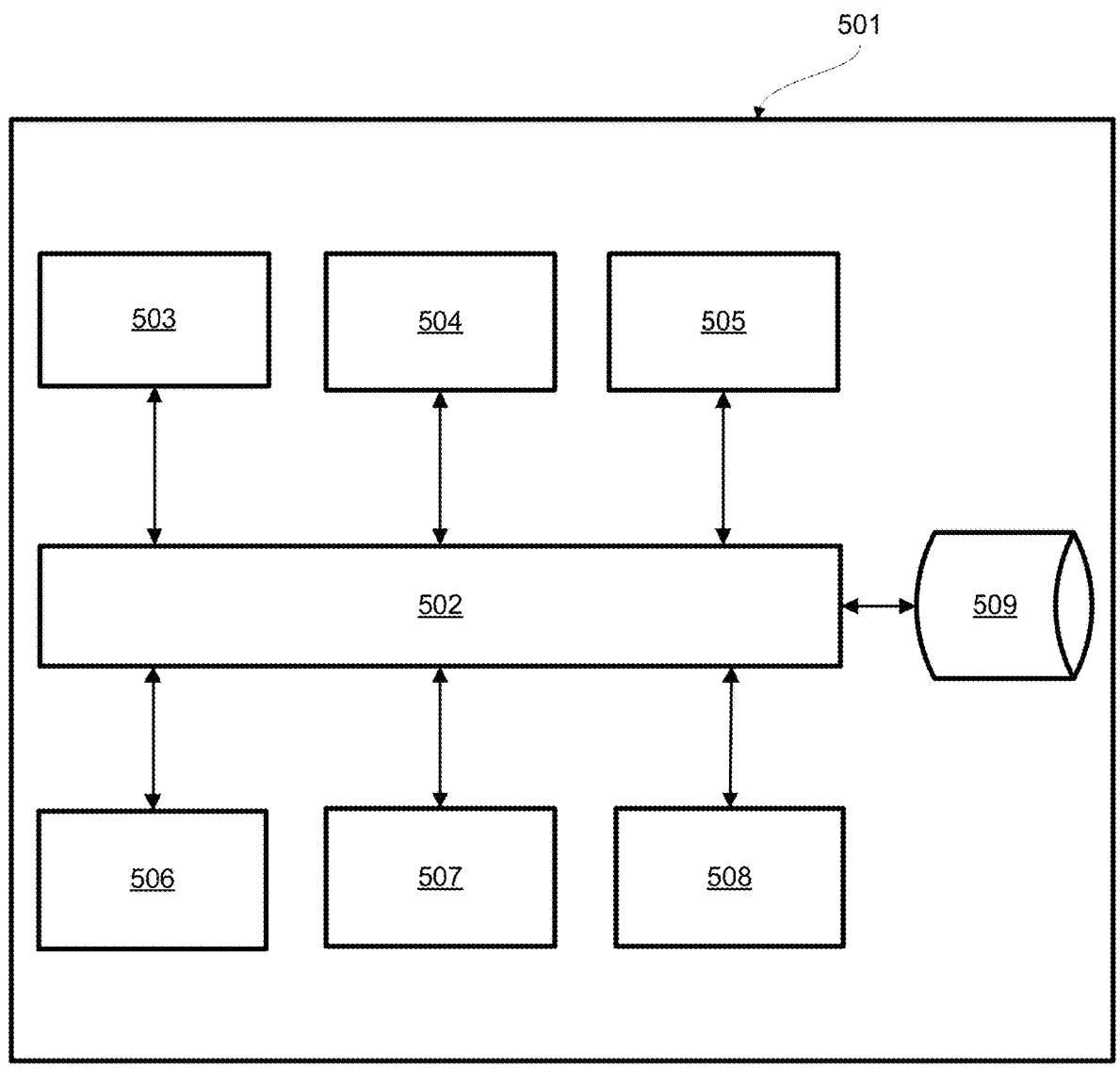
FIG. 5 illustrates an exemplary computer system.

FIG. 5 illustrates an exemplary computer system. Such a computer system could be used as computing server/node/device 12 of FIG. 1. The computer system 501 includes a bus 502 or other communication mechanism for communicating information, a processor 503 coupled to the bus 502 for processing information, and a memory 505 coupled to the bus 502 for dynamically and/or statically storing information. The computer system 501 can also include one or more co-processors 504 coupled to the bus 502, such as GPUs and/or FPGAs, for performing specialized processing tasks; a display 506 coupled to the bus 502, such as a cathode ray tube (CRT) or liquid crystal display (LCD), for displaying information to a computer user; an input device 507 coupled to the bus 502, such as a keyboard including alphanumeric and other keys, for communicating information and command selections to the processor 503; a cursor control device 508 coupled to the bus 502, such as a mouse, a trackball or cursor direction keys for communicating direction information and command selections to the processor 503 and for controlling cursor movement on display 506; and one or more storage devices 509 coupled to the bus 502, such as a magnetic disk or an optical disk, for storing information and instructions. The memory 505 may include a random access memory (RAM) or other dynamic storage device and/or a read only memory (ROM) or other static storage device. Such an exemplary computer system with suitable software may be used to perform the embodiments described herein. More generally, in various embodiments, one or more features of the teachings and/or embodiments described herein may be performed or implemented using appropriately configured and/or programmed hardware and/or or software elements.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of teachings and/or embodiments described herein may be performed or implemented using an appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed, clustered, remote, or cloud architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

Figure 6:
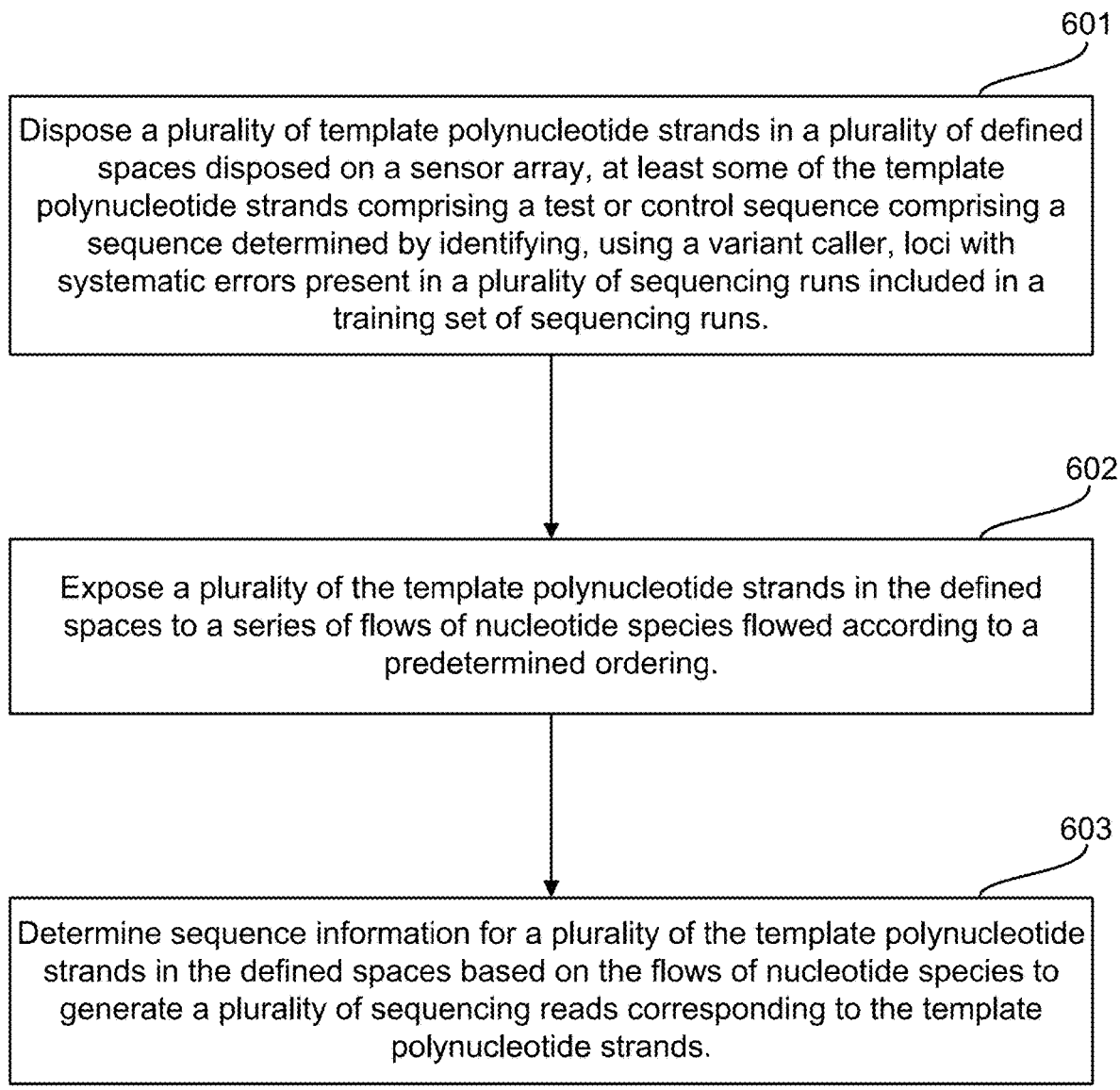
FIG. 6 illustrates an exemplary method for nucleic acid sequencing using control sequences.

FIG. 6 illustrates an exemplary method for nucleic acid sequencing using control sequences. In step 601, a user or component disposes a plurality of template polynucleotide strands in a plurality of defined spaces disposed on a sensor array, at least some of the template polynucleotide strands comprising a test or control sequence comprising a sequence determined by identifying, using a variant caller, loci with systematic errors present in a plurality of sequencing runs included in a training set of sequencing runs. Any suitable variant caller may be used, including the Germ-Line Variant Caller and the Torrent Variant Caller (TVC) Plug-ins for Ion Torrent™ sequencing technology, for example. In an embodiment, the variant caller may implement one or more features described in Hubbell et al., U.S. patent application Ser. No. 14/200,942, filed Mar. 7, 2014, which is incorporated by reference herein in its entirety. In step 602, a user or component exposes a plurality of the template polynucleotide strands in the defined spaces to a series of flows of nucleotide species flowed according to a predetermined ordering. Any suitable predetermined ordering may be used. For example, the predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG ACTG . . ."), may be based in whole or in part on some other pattern of reagent flows (such as, e.g., any of the various reagent flow orderings discussed in Hubbell et al., U.S. Pat. Appl. Publ. No. 2012/0264621, published Oct. 18, 2012, which is incorporated by reference herein in its entirety), and may also be based on some combination thereof. In step 603, a server or other computing means or resource determines sequence information for a plurality of the template polynucleotide strands in the defined spaces based on the flows of nucleotide species to generate a plurality of sequencing reads corresponding to the template polynucleotide strands. The sequence information may be determined using measured intensity values that may be related to voltage data indicative of hydrogen ion concentrations representative of a number of nucleotide incorporations responsive to each flowed nucleotide species or may include any other type of data (e.g., pyrophosphate, light, etc.) that could be representative of a number of nucleotide incorporations responsive to each flowed nucleotide species. Any suitable base calling method may be used, including as described in Davey et al., U.S. Pat. Appl. Publ. No. 2012/0109598, published on May 3, 2012, and/or Sikora et al., U.S. Pat. Appl. Publ. No. 2013/0060482, published on Mar. 7, 2013, which are all incorporated by reference herein in their entirety.

Design of Control Sequences

In various embodiments, control nucleic acid sequences (e.g., for use in sequencing-by-synthesis) may be designed based at least in part on length considerations. For example, control nucleic acid sequences may be designed to have a length in excess of 100 bases, such as at least 125 bases, at least 150 bases, at least 175 bases, at least 200 bases, at least 225 bases, at least 250 bases, or more. Such control nucleic acid sequences may be less oversensitive to errors compared to library reads than would be shorter control nucleic acid sequences (e.g., "short" sequences of 96 bases only allow one error when using a 50Q17 quality metric), and may therefore provide a more quantitative indication of run performance than shorter sequences.

In various embodiments, control nucleic acid sequences (e.g., for use in sequencing-by-synthesis) may be designed with content other than a relatively short series of homopolymers of only certain lengths. For example, control nucleic acid sequences may be designed with content that is not merely a series of homopolymers of length two, three, or four and no other length; or of homopolymers of length no more than 2; or of homopolymers of length no more than 1. Such control nucleic acid sequences with more complex content may be less sensitive to certain errors specific to particular homopolymer lengths or other phenomena such as pH drift, and may be better adapted to assess actual sequencing errors. In particular, such control nucleic acid sequences with more complex content may help provide improved determinations of general pass/fail criteria, may help support longer inserts and have similar performance/read length, and may provide sequences with single starting points that represent library read quality and that could start at multiple points of a given sequence.

In various embodiments, control nucleic acid sequences (e.g., for use in sequencing-by-synthesis) may be designed by identifying, using a variant caller, loci with systematic errors present in a plurality of sequencing runs included in a training set of sequencing runs. The control nucleic acid sequences may be generated by performing a set of sequencing runs for templates of a known library (e.g., *E. coli* DH10B, Lambda, synthetic sequences, etc.) under various conditions and analyzing an extent to which each of the runs is affected by one or more sequencing failure modes such as: systematic errors for high homopolymers in general, systematic errors for high homopolymers in specific contexts, and/or systematic errors for specific "difficult" sequences not involving high homopolymers. In an embodiment, control nucleic acid sequences may be generated using combinations of sequence fragments that contain multiple informative variants, such as context sequences that contain false positive variants (which may identified using variant calls made by a variant caller, as such calls would be false positives since the exact reference sequence is known). The particular combinations may be of a desired length, preferably above 100 bases. For example, the combinations may be 125, 150, 175, 200, 225, 250, or more bases in length (without adapters) comprising some segments that are known to be difficult to sequence for some known library. The combinations may be generated from identified segments in any suitable manner, including randomly in whole or in part. The size of the regions may vary and the location of the variant in the region may be at or near the center but that is not necessary. Once the regions have been selected, they may be stitched together to form a desired number of sequences of some desired length (e.g., sets of 10 regions of 20-base fragments could be stitched together to form 200-base control sequences).

Figure 7:
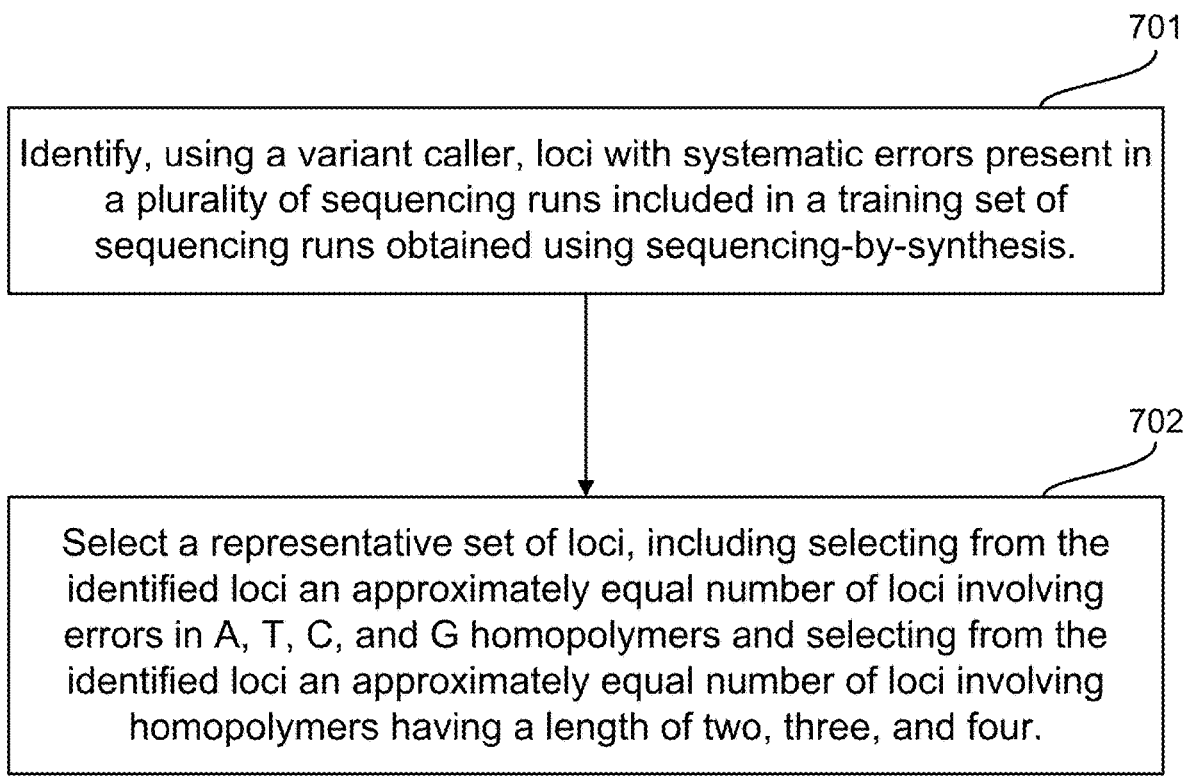
FIG. 7 illustrates an exemplary method for generating control sequences.

FIG. 7 illustrates an exemplary method for generating control sequences. In step 701, a server or other computing means or resource identifies, using a variant caller, loci with systematic errors present in a plurality of sequencing runs included in a training set of sequencing runs obtained using sequencing-by-synthesis. In step 702, the server or other computing means or resource selects a representative set of loci, including selecting from the identified loci an approximately equal number of loci involving errors in A, T, C, and G homopolymers and selecting from the identified loci an approximately equal number of loci involving homopolymers having a length of two, three, and four.

Figure 8:
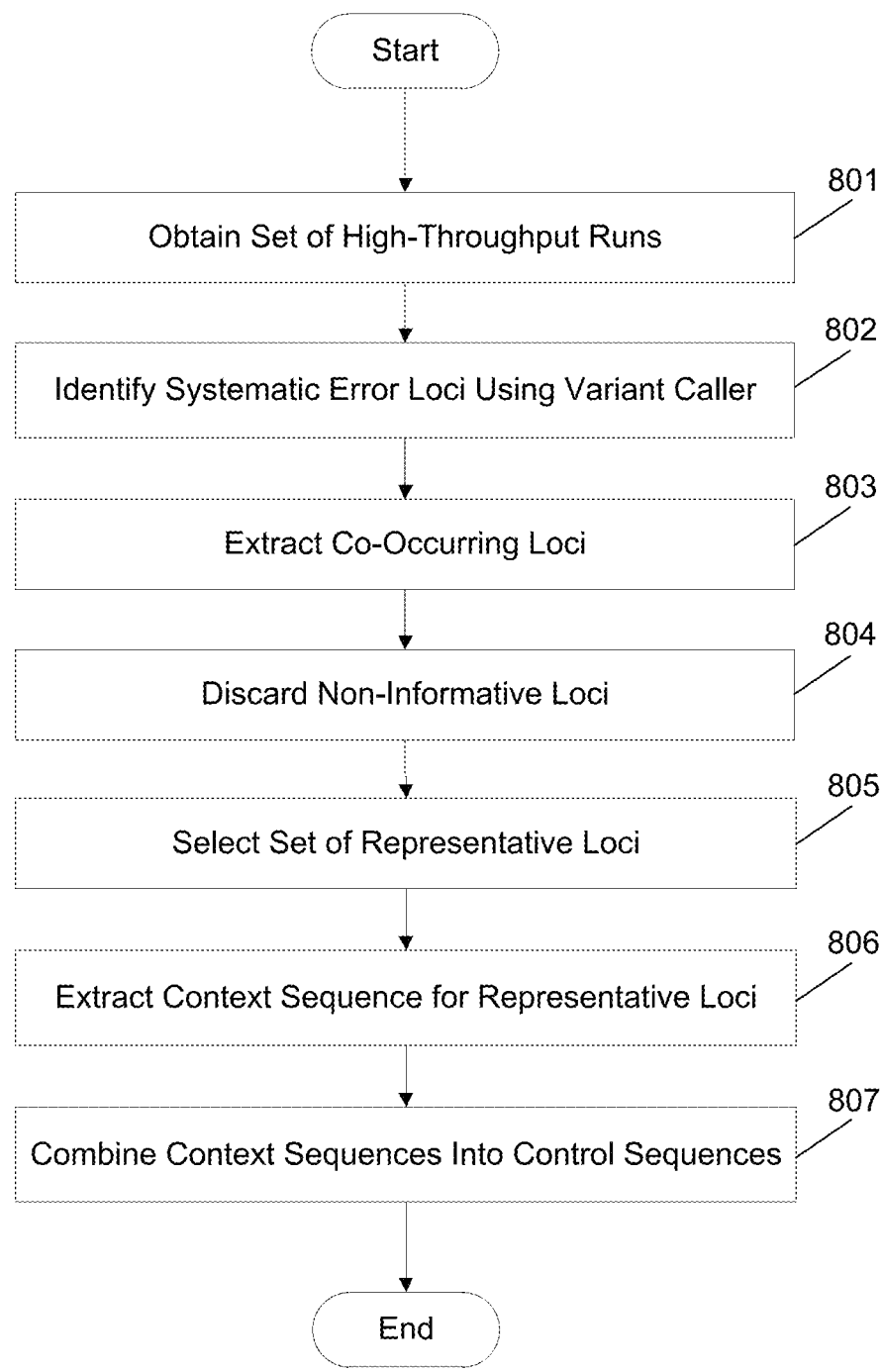
FIG. 8 illustrates an exemplary method for generating control sequences.

FIG. 8 illustrates an exemplary method for generating control sequences. In step 801, a user or component obtains a set of high-throughput runs for a known reference library (e.g., *E. coli* DB10H). The run data may include, e.g., measured intensity values that may be related to voltage data indicative of hydrogen ion concentrations representative of a number of nucleotide incorporations or may include any other type of data (e.g., pyrophosphate, light, etc.) that could otherwise be representative of a number of nucleotide incorporations. The data may be processed and analyzed to make base calls using any suitable base calling method or approach, as discussed above. In step 802, a server or other computing means or resource identifies systematic error loci in the runs using a variant caller. Any suitable variant caller may be used, as discussed above. In step 803, the server or other computing means or resource extracts co-occurring loci. For example, loci that are present in at least a minimal number of runs (e.g., at least 3 runs) may be extracted. In some cases, that minimal threshold may be only two or may be larger (e.g., at least 4 runs, at least 5 runs, or more), and the threshold may be selected depending on the sample size. In step 804, the server or other computing means or resource discards non-informative loci. For example, loci that are present in more than a maximal number of runs (e.g., more than 20 runs) may suggest the presence of sources of error other than the ones contemplated in the present design process and may thus be discarded. In some cases, that maximal threshold may be smaller or larger than 20, and the threshold may be selected depending on the sample size. In step 805, the server or other computing means or resource selects a set of representative loci from the loci remaining after steps 803 and 804. For example, the set of representative loci may be selected to comprise an approximately equal number of loci involving errors in A, T, C, and G homopolymers and an approximately equal number of loci involving homopolymers having a length of two, three, and four. In some cases, an approximately equal number of certain homopolymer types and/or lengths may be an equal number of each type and/or length, however, depending on the data and variant calls that may not always be possible.

In some cases, an approximately equal number of certain homopolymer types and/or lengths may correspond to situations where at least two of the homopolymer types and/or lengths are equal. In some cases, an approximately equal number of certain homopolymer types and/or lengths may correspond to situations where at least three of the homopolymer types and/or lengths are equal. In other cases, an approximately equal number of certain homopolymer types and/or lengths may correspond to situations where none of each homopolymer type and/or length is allowed to have a number further distant from the mean or median of the numbers of the homopolymer types and/or lengths than some pre-defined threshold. In some cases, different combinations of homopolymer types or lengths could be used (e.g., an approximately equal number of loci involving homopolymers having a length of two, four, and six; or having a length of three, four, and five; etc.) In step 806, the server or other computing means or resource extracts a context sequence from the known reference library for each of the representative loci, which may be positioned at or near the center of its corresponding context sequence although that is not necessary and other positions within the context sequence are also possible. In step 807, the extracted context sequences are combined into longer control sequences, which combination may be done in any suitable way, including by manual inspection/selection or randomly in whole or in part.

Figure 9A:
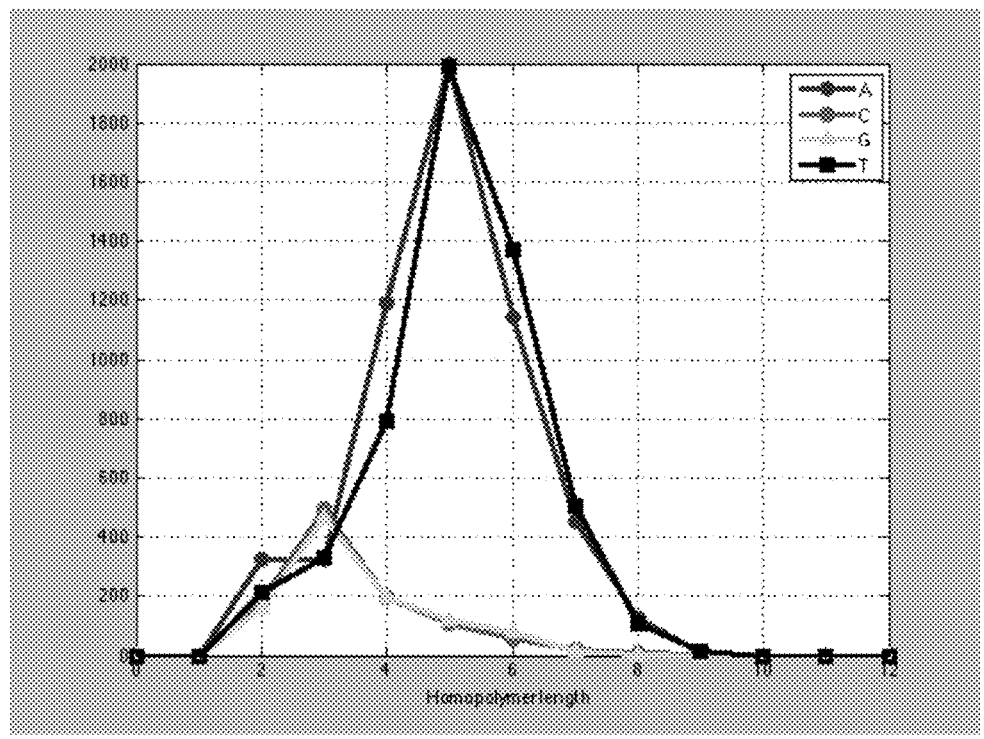
FIGS. 9A and 9B show plots of unique variants according to nucleotide and homopolymer length.
Figure 9B:
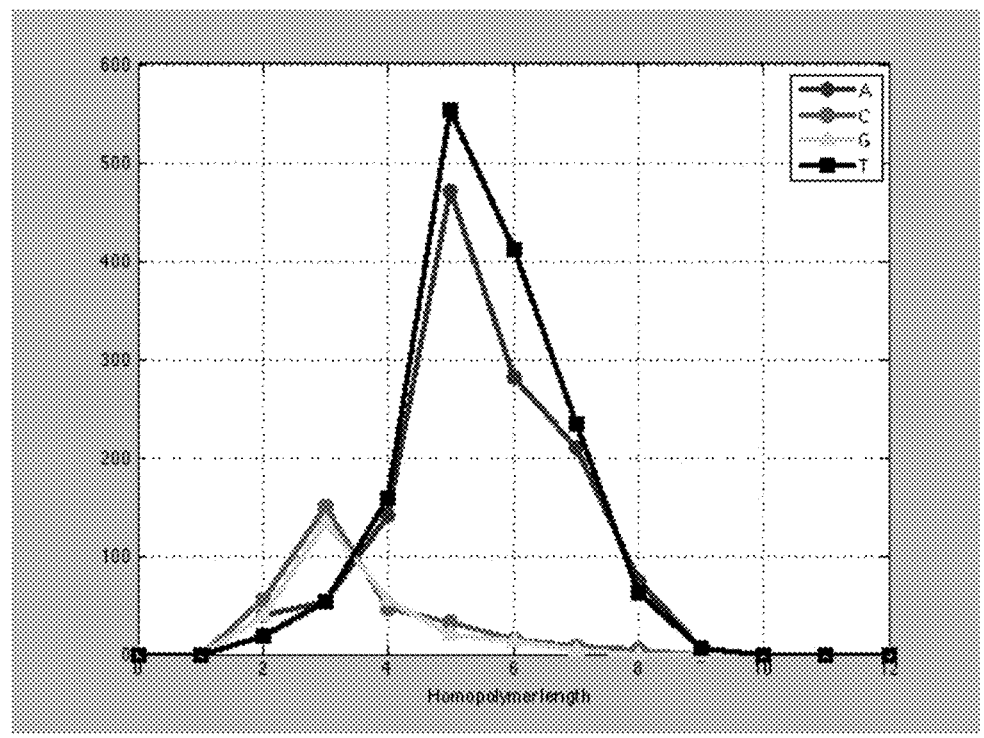

In an example, control nucleic acid sequences were generated using the following steps. In step 1, a set of 94 high-throughput *E. coli* DH10B runs were obtained using the Ion PGM™ system implementing Ion Torrent™ sequencing technology. In step 2, each of the 94 runs was analyzed to identify DH10B loci with systematic errors by running a variant caller on the sequencing data (as mentioned previously, since the DH10B sample has no variants relative to the reference, every called variant is in fact a false positive caused by systematic errors). Here, variant calls were obtained for the runs using the Germ-Line Variant Caller Plug-in, however, any suitable variant caller could be used also. Altogether, the runs contained 32,110 variant calls and 13,044 unique variants. FIG. 9A shows a plot of unique variants according to nucleotide (A, C, G, or T) and homopolymer length (0-mer through 12-mer). Among the unique variants, 3,464 were called in at least 3 runs and 99 were called in at least 20 runs. In step 3, each of the identified DH10B loci was analyzed to determine whether it is present in at least three of the runs (in other words, co-occurring variant locations were identified). In step 4, informative variant locations were pre-selected from the loci identified in step 3 by discarding loci with variant calls in more than 20 of the runs (if a given locus was called a variant on too many runs, that locus is likely to be systematically called differently from the reference for reasons other than the error modes of interest here). FIG. 9B shows a plot of a subset of unique variants according to nucleotide (A, C, G, or T) and homopolymer length (0-mer through 12-mer). Shown in FIG. 9B are unique variants present in at least 3 runs and at most 20 runs. In step 5, a representative set of 100 loci was selected from the loci remaining after steps 3 and 4 by selecting an approximately equal number of loci involving errors in A, T, C, and G homopolymers, and an approximately equal number of loci involving 2-mers, 3-mers, and 4-mers. Here, the loci included 25 loci for each of A, T, C, and G homopolymers, and 39 loci for each of homopolymers of length 3 and 4 with 22 loci for homopolymers of length 2. Two additional loci having consecutive homopolymers of length 5 and 2 were additionally identified. In step 6, for each locus in the representative set of loci selected in step 5, a 25-base context sequence containing that locus was extracted, with the locus being at or near the center of the context sequence. Appendix I includes a list of 102 exemplary 25-base context sequence fragments together with the position of the middle locus in the DH10B genome, the homopolymer locus (see boldface/underline) for which the context sequence was extracted, and the type and length of the homopolymer locus for which the context sequence was extracted. In step 7, 100 of the context sequences extracted in step 6 were combined in silico into groups of ten to form ten control sequences of 250 bases. Appendix II includes a list of 10 control sequences together with the homopolymer loci (see boldface/underline) for which each of the context sequences in the control sequence was extracted, and the types and lengths of the homopolymer locus for which each of the context sequences in the control sequence was extracted. For example, the first control sequence is a combination of context sequences extracted for A homopolymers of lengths 2, 3, and 4; G homopolymers of lengths 2, 3, and 4; C homopolymers of lengths 3 and 4; and T homopolymers of lengths 3 and 4. The control sequences may of course include additional homopolymers other than the ones used to extract the context sequences they comprise; only the homopolymers used to extract the context sequences are shown boldface/underline and counted in the loci types/lengths column of Appendix II.

In various examples, control sequences generated as described above may be used without further selection or they may be further tested empirically in various ways to select a smaller subset of desired control sequences for use in particular applications or in sequencing-by-synthesis generally. As part of such testing and/or sequencing, the control sequences may be synthesized and attached at one end to a sequencing adapter that may include a sequencing key identifying the sequence as a control sequence (e.g., CCAT CTCA TCCC TGCG TGTC TCCG ACAT CG, SEQ ID NO: 113), and at the other end to another adapter sequence (e.g., ATCA CCGA CTGC CCAT AGAG AGGA AAGC GGAG GCGT AGTG G, SEQ ID NO: 114). Sequence synthesis and attachment may be done using any suitable method known in the art. A series of feasibility runs may then be performed using any suitable sequencing technology, and a subset of desired control sequences may be selected based on an analysis of the runs. In some cases, some of the runs may be performed in ideal situations while others are intentionally performed under inadequate situations (e.g., by intentionally using an inadequate pH level when using Ion Torrent™ sequencing technology), and comparison of the behavior of the control sequences across ideal/inadequate situations may be used to identify control sequences that better conform or are more consistent with the underlying experimental situation. Selection of a particular subset of control sequences may be based on various accuracy criteria (e.g., mean read length, fraction of aligned reads, error(s) at particular positions, or other quality metrics), or platform-specific parameters or phenomena (e.g., pH drift), or other error sources or error-reducing goals or objectives, or some combination thereof.

According to an exemplary embodiment, there is provided a method for nucleic acid sequencing, comprising: (a) disposing a plurality of template polynucleotide strands in a plurality of defined spaces disposed on a sensor array, at least some of the template polynucleotide strands comprising a test or control sequence; (b) exposing a plurality of the template polynucleotide strands in the defined spaces to a series of flows of nucleotide species flowed according to a predetermined ordering; and (c) determining sequence information for a plurality of the template polynucleotide strands in the defined spaces based on the flows of nucleotide species to generate a plurality of sequencing reads corresponding to the template polynucleotide strands, wherein the test or control sequence comprises a sequence determined by identifying, using a variant caller, loci with systematic errors present in a plurality of sequencing runs included in a training set of sequencing runs.

In such a method, the test or control sequence may comprise a sequence further determined by finding co-occurring variant locations present in at least three sequencing runs included in a training set of sequencing runs. The test or control sequence may comprise a sequence further determined by pre-selecting informative variant locations. The test or control sequence may comprise a sequence further determined by discarding co-occurring variant locations present in more than twenty sequencing runs included in a training set of sequencing runs. The test or control sequence may comprise a sequence further determined by selecting a representative set of loci, including selecting from the set of identified loci an approximately equal number of loci involving errors in A, T, C, and G homopolymers. The test or control sequence may further comprise a sequence further determined by selecting from the set of identified loci an approximately equal number of loci involving homopolymers having a length of two, three, and four. The test or control sequence may comprise a sequence further determined by extracting a context sequence containing each locus in the representative set of loci. The test or control sequence may comprise a sequence further determined by combining in silico the extracted context sequences. The test or control sequence may comprise a sequence further determined by attaching one or more sequencing adapters to the combined sequence. The test or control sequence may comprise a sequence further determined by finding co-occurring variant locations present in at least three and no more than twenty sequencing runs included in a training set of sequencing runs. The test or control sequence may comprise a sequence further determined by finding co-occurring variant locations present in at least five and no more than fifteen sequencing runs included in a training set of sequencing runs.

According to an exemplary embodiment, there is provided a kit for nucleic acid sequencing, comprising: a plurality of test or control sequences each comprising a sequence determined by identifying, using a variant caller, loci with systematic errors present in a plurality of sequencing runs included in a training set of sequencing runs obtained using sequencing-by-synthesis, wherein the test or control sequences each comprise a sequence further determined by selecting a representative set of loci, including selecting from the identified loci an approximately equal number of loci involving errors in A, T, C, and G homopolymers and selecting from the identified loci an approximately equal number of loci involving homopolymers having a length of two, three, and four.

According to an exemplary embodiment, there is provided a system, including: a plurality of template polynucleotide strands disposed in a plurality of defined spaces disposed on a sensor array, at least some of the template polynucleotide strands comprising a test or control sequence, wherein the test or control sequence comprises a sequence determined by identifying, using a variant caller, loci with systematic errors present in a plurality of sequencing runs included in a training set of sequencing runs; a machine-readable memory; and a processor configured to execute machine-readable instructions, which, when executed by the processor, cause the system to perform a method for nucleic acid sequencing, comprising: (a) exposing a plurality of the template polynucleotide strands in the defined spaces to a series of flows of nucleotide species flowed according to a predetermined ordering; and (b) determining sequence information for a plurality of the template polynucleotide strands in the defined spaces based on the flows of nucleotide species to generate a plurality of sequencing reads corresponding to the template polynucleotide strands.

In such a system, the test or control sequence may comprise a sequence further determined by selecting a representative set of loci, including selecting from the identified loci an approximately equal number of loci involving errors in A, T, C, and G homopolymers and selecting from the identified loci an approximately equal number of loci involving homopolymers having a length of two, three, and four.

According to an exemplary embodiment, there is provided a method for designing test or control sequences, comprising: identifying, using a variant caller, loci with systematic errors present in a plurality of sequencing runs included in a training set of sequencing runs obtained using sequencing-by-synthesis; and selecting a representative set of loci, including selecting from the identified loci an approximately equal number of loci involving errors in A, T, C, and G homopolymers and selecting from the identified loci an approximately equal number of loci involving homopolymers having a length of two, three, and four.

In such a method, the test or control sequence may comprise a sequence further determined by finding co-occurring variant locations present in at least three sequencing runs included in a training set of sequencing runs. The test or control sequence may comprise a sequence further determined by pre-selecting informative variant locations. The test or control sequence may comprise a sequence further determined by discarding co-occurring variant locations present in more than twenty sequencing runs included in a training set of sequencing runs. The test or control sequence may comprise a sequence further determined by extracting a context sequence containing each locus in the representative set of loci. The test or control sequence may comprise a sequence further determined by combining in silico the extracted context sequences. The test or control sequence may comprise a sequence further determined by attaching one or more sequencing adapters to the combined sequence. The test or control sequence may comprise a sequence further determined by finding co-occurring variant locations present in at least three and no more than twenty sequencing runs included in a training set of sequencing runs. The test or control sequence may comprise a sequence further determined by finding co-occurring variant locations present in at least five and no more than fifteen sequencing runs included in a training set of sequencing runs.

Unless otherwise specifically designated herein, terms, techniques, and symbols of biochemistry, cell biology, genetics, molecular biology, nucleic acid chemistry, nucleic acid sequencing, and organic chemistry used herein follow those of standard treatises and texts in the relevant field.

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

APPENDIX I

| Position | Context Sequence Fragment | Type | Length | SEQ ID NO: |
|---|---|---|---|---|
| 3059197 | GATGCAGCACCGAAGGCTGAATATC | A | 2 | SEQ ID NO: 1 |
| 3620936 | TCTCAGGTTACGAAGGCGGTGCCAA | A | 2 | SEQ ID NO: 2 |
| 1321265 | TTGATCGACTTTAACGTCCGTGCGG | A | 2 | SEQ ID NO: 3 |
| 454206 | AGCCCCGGCTGTAACGTTTTGGTAT | A | 2 | SEQ ID NO: 4 |
| 1505557 | GTTTGCCGAGGCAATATATGTCCGG | A | 2 | SEQ ID NO: 5 |
| 3930414 | CCGCCGAAGGCCAACCCCAGTTTGA | A | 2 | SEQ ID NO: 6 |
| 3665932 | ACAGCGGCGGGAAATTTCCCACCTG | A | 3 | SEQ ID NO: 7 |
| 4028930 | GTGGGTCAGCGAAACGTTTCGCTGA | A | 3 | SEQ ID NO: 8 |
| 3032774 | AGCGGAACAGTAAATTTACGGCAGA | A | 3 | SEQ ID NO: 9 |
| 2183647 | GTTATGAACCCAAAGTCAGCCGTGA | A | 3 | SEQ ID NO: 10 |
| 2568253 | GACTGCCCTTTAAACCTGTACCCAC | A | 3 | SEQ ID NO: 11 |
| 2903059 | TACTGGCAAATAAAGTACGTTCCAC | A | 3 | SEQ ID NO: 12 |
| 992689 | AAGAGCGTCGTAAAGTATTGCAGGT | A | 3 | SEQ ID NO: 13 |
| 945598 | TCAGGCGGCGGAAAGCGTGATTGAC | A | 3 | SEQ ID NO: 14 |
| 1204000 | CTGACGCTGCCAAACGCCGACCGCG | A | 3 | SEQ ID NO: 15 |
| 4284712 | ATGCGCGCGTTAAAGTGCGTATCAC | A | 3 | SEQ ID NO: 16 |
| 1221988 | ATGGTTACTTTAAAACCGGATTAAT | A | 4 | SEQ ID NO: 17 |

APPENDIX I-continued

| Position | Context Sequence Fragment | Type | Length | SEQ ID NO: |
|---|---|---|---|---|
| 2538868 | CATCAGGCACCAAAAGAGTATGGCG | A | 4 | SEQ ID NO: 18 |
| 3186626 | ACTTCGGCACCAAAAGCATTGGCGT | A | 4 | SEQ ID NO: 19 |
| 4566931 | GCGGGAAGGGGAAAATCCATGCTGA | A | 4 | SEQ ID NO: 20 |
| 4235391 | GTTCGTCCGTGAAAATAAGAGTCAC | A | 4 | SEQ ID NO: 21 |
| 887336 | ATTTAAGTGAGAAAACCGGCAGCCA | A | 4 | SEQ ID NO: 22 |
| 3480357 | CGAAATTTGATAAAATCCCGCTCTT | A | 4 | SEQ ID NO: 23 |
| 2102606 | GCTTGATCAGGAAAAGTTTGGTATC | A | 4 | SEQ ID NO: 24 |
| 4286302 | GTCCGGCACTGAAAATCGTTGATGC | A | 4 | SEQ ID NO: 25 |
| 1469524 | GCTGGCGGAGCCTTCAGTCTATTTT | T | 2 | SEQ ID NO: 26 |
| 59306 | CTGGAACGCCCCTTCAACCTTAGCA | T | 2 | SEQ ID NO: 27 |
| 3395983 | AAGGCGCAGGGTTTGCAGAGCTGTT | T | 3 | SEQ ID NO: 28 |
| 2781684 | GCCACCAGCCCTTTGCTTTCCAGTG | T | 3 | SEQ ID NO: 29 |
| 4533299 | GTACCGGCAAATTTGCCGCCGTAAG | T | 3 | SEQ ID NO: 30 |
| 1817146 | GTCGGCGCAAATTTGCAACCAGAAG | T | 3 | SEQ ID NO: 31 |
| 160766 | GCGTGACCAAATTTGGTGCAGCGCC | T | 3 | SEQ ID NO: 32 |
| 3665935 | GCGGCGGGAAATTTCCCACCTGATA | T | 3 | SEQ ID NO: 33 |
| 197121 | CTCGCGGTAAATTTACCGAAGCACA | T | 3 | SEQ ID NO: 34 |
| 1554427 | TCCCAAACCGGTTTCGTTTAATAAT | T | 3 | SEQ ID NO: 35 |
| 2039554 | TGGCGGCGAAATTTCGCGCCAGCGG | T | 3 | SEQ ID NO: 36 |
| 4180498 | TCCGTTACACCTTTTCCACATTCAC | T | 4 | SEQ ID NO: 37 |
| 881464 | TGTGTCAGGGCTTTTGGTTCTCCCT | T | 4 | SEQ ID NO: 38 |
| 2659290 | TCTGCAATTCATTTTGCATATAGCC | T | 4 | SEQ ID NO: 39 |
| 4099761 | CATAACTATTGTTTTGATGAATCAG | T | 4 | SEQ ID NO: 40 |
| 4497018 | GTATCGCCAGCTTTTGCAAACGCCC | T | 4 | SEQ ID NO: 41 |
| 2308230 | ACGCTGCATCGTTTTCATCTTTAAA | T | 4 | SEQ ID NO: 42 |
| 2425780 | AGATAGCTCCCTTTTGGCATGAAGA | T | 4 | SEQ ID NO: 43 |
| 4073210 | TGTTGAACTACTTTTCCTGATATGT | T | 4 | SEQ ID NO: 44 |
| 3385917 | AACCAGCACTCTTTTCATGGCTATC | T | 4 | SEQ ID NO: 45 |
| 955284 | ACAGGACGCCATTTTGCCGACTCCC | T | 4 | SEQ ID NO: 46 |
| 1018410 | TCTGGCGGCAATTTTGCTGATGGAT | T | 4 | SEQ ID NO: 47 |
| 2212298 | TCAATGGTGACTTTTGCCGTTCCCG | T | 4 | SEQ ID NO: 48 |
| 2380894 | CTGCTGCCAGATTTTCACCTGCTGA | T | 4 | SEQ ID NO: 49 |
| 1765974 | CTTTGACACCATTTTCCGTAGTGAA | T | 4 | SEQ ID NO: 50 |
| 4596308 | GTTCGAGTCCGGCCTTCGGCACCAA | C | 2 | SEQ ID NO: 51 |
| 1638520 | AGGGATGGGACGCCTGTTTGCCATC | C | 2 | SEQ ID NO: 52 |
| 821095 | GATCGATCCAGGCCTAATCGATCGG | C | 2 | SEQ ID NO: 53 |
| 3365511 | ACGCTTATCAGGCCTACGCCATCTC | C | 2 | SEQ ID NO: 54 |
| 777133 | GTGGTCAGCGAGGCCACGGGTCATCA | C | 2 | SEQ ID NO: 55 |
| 2748576 | AGCAGGTGACGGCCTTCATGATCGG | C | 2 | SEQ ID NO: 56 |

APPENDIX I-continued

| Position | Context Sequence Fragment | Type | Length | SEQ ID NO: |
|---|---|---|---|---|
| 3298858 | TTGCGGCGGTAGCCAGCTGGAAGGA | C | 2 | SEQ ID NO: 57 |
| 4676206 | CGATCGTCGCGGCCTGAATACCTGG | C | 2 | SEQ ID NO: 58 |
| 2643681 | GGAAAGCGATGGCCTACGGCGAGCG | C | 2 | SEQ ID NO: 59 |
| 4466413 | TACCTGCGCCGCCCTGGTAGACGTC | C | 3 | SEQ ID NO: 60 |
| 3778832 | AGGCGACAATGCCCTGGTCTTTCGC | C | 3 | SEQ ID NO: 61 |
| 52406 | GGGCTAAGTGGCCCTGGTGGACTCG | C | 3 | SEQ ID NO: 62 |
| 792761 | AGGCAATCGAGCCCAGATGCCGGAT | C | 3 | SEQ ID NO: 63 |
| 4497766 | CGTTGATTCTGCCCTTATTTACAAA | C | 3 | SEQ ID NO: 64 |
| 1503858 | GAATAATCCAGCCCGCCAGGCATGG | C | 3 | SEQ ID NO: 65 |
| 2926403 | CAGGCAAGCCGCCCAGGTGCTCACA | C | 3 | SEQ ID NO: 66 |
| 1857907 | GTGTTTATCATCCCTATTGCTTTGC | C | 3 | SEQ ID NO: 67 |
| 3638552 | TATGGAAGCGGCCCAGATAAGCCAG | C | 3 | SEQ ID NO: 68 |
| 2775787 | TCAACGTGAAGCCCTGTTTAACGCT | C | 3 | SEQ ID NO: 69 |
| 4167872 | TGATATTCCTGCCCCTGATAGCGGT | C | 4 | SEQ ID NO: 70 |
| 2160039 | ATGCCGCCAGTCCCCTGATGACCCG | C | 4 | SEQ ID NO: 71 |
| 4275966 | CGGTCGTGCGACCCCGGTAGAGCTG | C | 4 | SEQ ID NO: 72 |
| 2878452 | TGTTATATCTGCCCCGATAAAACGG | C | 4 | SEQ ID NO: 73 |
| 3704512 | AAGCCAATCAGCCCCTATCAACCGC | C | 4 | SEQ ID NO: 74 |
| 2039072 | GTCACCTGCTGCCCCACGTGGGACA | C | 4 | SEQ ID NO: 75 |
| 3886677 | CACAGGTGATATGGCCTTCGCCAGA | G | 2 | SEQ ID NO: 76 |
| 4257151 | AGCTACCCGATAGGCTTCCGCCATC | G | 2 | SEQ ID NO: 77 |
| 2009720 | TACGACTGCGAAGGCTTCTTCGTTG | G | 2 | SEQ ID NO: 78 |
| 2018580 | TGGGGCGGACAAGGCACTCGCGCCG | G | 2 | SEQ ID NO: 79 |
| 3978844 | CAACGGGTTATAGGCACCGCCAGGG | G | 2 | SEQ ID NO: 80 |
| 2937614 | TAGCGGTAAACGGGCTACCGGTATC | G | 3 | SEQ ID NO: 81 |
| 1813728 | TGATTGCAACAGGGCAAATTGCGCA | G | 3 | SEQ ID NO: 82 |
| 2716017 | TGCATGAGGTCGGGTTGAATATCAA | G | 3 | SEQ ID NO: 83 |
| 4190007 | TTTCTGTTCCAGGGCTTCCGCCACC | G | 3 | SEQ ID NO: 84 |
| 1217166 | ATGACGCCAGAGGGCTGGAGATGCA | G | 3 | SEQ ID NO: 85 |
| 906184 | TCGATCCTTGAGGGATGATTGCATT | G | 3 | SEQ ID NO: 86 |
| 2247497 | TGCGGCATACTGGGCTTCCGTATGC | G | 3 | SEQ ID NO: 87 |
| 8186 | TGATATCATCAGGGCAGACCGGTTA | G | 3 | SEQ ID NO: 88 |
| 2795077 | CACCAGAATCAGGGCAAACATATTC | G | 3 | SEQ ID NO: 89 |
| 1807015 | CCTGGTCTGGAGGGCAATACGCCCT | G | 3 | SEQ ID NO: 90 |
| 1352099 | ATCACCGAATCGGGGACCACCGCCA | G | 4 | SEQ ID NO: 91 |
| 1048275 | GCCCATAAATTGGGGCTGATCTCCA | G | 4 | SEQ ID NO: 92 |
| 4685037 | ACAGGCTAAGAGGGGCCGGACACCC | G | 4 | SEQ ID NO: 93 |
| 968215 | CCCTGAAGGCCGGGGCAGCCCACAT | G | 4 | SEQ ID NO: 94 |
| 193277 | GATTCGGCAAAGGGGAGATACGGTT | G | 4 | SEQ ID NO: 95 |

APPENDIX I-continued

| Position | Context Sequence Fragment | Type | Length | SEQ ID NO: |
|---|---|---|---|---|
| 4561118 | TATAGAGGATCGGGGCCACGCGCGC | G | 4 | SEQ ID NO: 96 |
| 2141910 | TCTTGCACAAAGGGGAGAAGCAATT | G | 4 | SEQ ID NO: 97 |
| 4373401 | GAACGCTATCAGGGGCAAGTTTGCA | G | 4 | SEQ ID NO: 98 |
| 4429478 | CTTCCTCGATTGGGGCTGGCGTATT | G | 4 | SEQ ID NO: 99 |
| 1925107 | GGAATCGCCCTGGGGCGGCGCACAA | G | 4 | SEQ ID NO: 100 |
| 3147535 | TATCCAAATTTTTGGCCGTTCACTG | G | 2 | SEQ ID NO: 101 |
| 364140 | TTTGCTGGAAAAATTGCGCGCCAAA | T | 2 | SEQ ID NO: 102 |

APPENDIX II

| Control Sequence | Loci Types (Lengths) | SEQ ID NO: |
|---|---|---|
| GATGCAGCACCGAAGGCTGAATATC<br>TAGCGGTAAACGGGCTACCGGTATC<br>TGATATTCCTGCCCCTGATAGCGGT<br>GCCACCAGCCCTTTGCTTTCCAGTG<br>CATCAGGCACCAAAAGAGTATGGCG<br>TACCTGCGCCGCCCTGGTAGACGTC<br>ACAGGCTAAGAGGGGCCGGACACCC<br>GTTATGAACCCAAAGTCAGCCGTGA<br>CATAACTATTGTTTTGATGAATCAG<br>AGCTACCCGATAGGCTTCCGCCATC | A (2, 3, and 4)<br>G (2, 3, and 4)<br>C (3 and 4)<br>T (3 and 4) | SEQ ID NO: 103 |
| GCTGGCGGAGCCTTCAGTCTATTTT<br>GGGCTAAGTGGCCCTGGTGGACTCG<br>ATGGTTACTTTAAAACCGGATTAAT<br>TGATTCAACAGGGCAAATTGCGCA<br>TGTGTCAGGGCTTTTGGTTCTCCCT<br>AGCGGAACAGTAAATTTACGGCAGA<br>CGGTCGTGCGACCCCGGTAGAGCTG<br>GTCGGCGCAAATTTGCAACCAGAAG<br>CCCTGAAGGCCGGGGCAGCCCACAT<br>AGGGATGGGACGCCTGTTTGCCATC | A (3 and 4)<br>G (3 and 4)<br>C (2, 3, and 4)<br>T (2, 3, and 4) | SEQ ID NO: 104 |
| GTTCGAGTCCGGCCTTCGGCACCAA<br>AAGGCGCAGGGTTTGCAGAGCTGTT<br>ATCACCGAATCGGGGACCACCGCCA<br>GTGGGTCAGCGAAACGTTTCGCTGA<br>ATGCCGCCAGTCCCCTGATGACCCG<br>TGCATGAGGTCGGGTTGAATATCAA<br>TCTGCAATTCATTTTGCATATAGCC<br>AGGCAATCGAGCCCAGATGCCGGAT<br>GCGGGAAGGGGAAAATCCATGCTGA<br>CTGGAACGCCCTTCAACCTTAGCA | A (3 and 4)<br>G (3 and 4)<br>C (2, 3, and 4)<br>T (2, 3, and 4) | SEQ ID NO: 105 |
| CACAGGTGATATGGCCTTCGCCAGA<br>ACAGCGGCGGAAATTTCCCACCTG<br>TCCGTTACACCTTTTCCACATTCAC<br>AGGCGACAATGCCCTGGTCTTTCGC<br>GCCCATAAATTGGGGCTGATCTCCA<br>GTACCGGCAAATTTGCCGCCGTAAG<br>ACTTCGGCACCAAAAGCATTGGCGT<br>TTTCTGTTCCAGGGCTTCCGCCACC<br>TGTTATATCTGCCCCGATAAAACGG<br>TCTCAGGTTACGAAGGCGGTGCCAA | A (2, 3, and 4)<br>G (2, 3, and 4)<br>C (3 and 4)<br>T (3 and 4) | SEQ ID NO: 106 |
| GACTGCCCTTTAAACCTGTACCCAC<br>TCGATCCTTGAGGGATGATTGCATT<br>CAGGCAAGCCGCCCAGGTGCTCACA<br>TCCCAAACCGGTTTCGTTTAATAAT<br>GATTCGGCAAAGGGGAGATACGGTT<br>ACGCTGCATCGTTTTCATCTTTAAA<br>CGAAATTTGATAAAATCCCGCTCTT<br>AGCAGGTGACGGCCTTCATGATCGG<br>TTGATCGACTTTAACGTCCGTGCGG<br>ACAGGACGCCATTTTGCCGACTCCC | A (2, 3, and 4)<br>G (3 and 4)<br>C (2 and 3)<br>T (3, 4, and 4) | SEQ ID NO: 107 |
| GCGTGACCAAATTTGGTGCAGCGCC | A (2, 3, and 4) | SEQ ID NO: 108 |

APPENDIX II-continued

| Control Sequence | Loci Types (Lengths) | SEQ ID NO: |
|---|---|---|
| GAATAATCCAGCCCGCCAGGCATGG<br>AAGAGCGTCGTAAAGTATTGCAGGT<br>TGATATCATCAGGGCAGACCGGTTA<br>AAGCCAATCAGCCCCTATCAACCGC<br>TATAGAGGATCGGGGCCACGCGCGC<br>AGATAGCTCCCTTTTGGCATGAAGA<br>GCTTGATCAGGAAAAGTTTGGTATC<br>AACCAGCACTCTTTTCATGGCTATC<br>AGCCCCGGCTGTAACGTTTTGGTAT | G (3 and 4)<br>C (3 and 4)<br>T (3, 4, and 4) | |
| CGTTGATTCTGCCCTTATTTACAAA<br>GCGGCGGGAAATTTCCCACCTGATA<br>TGCGGCATACTGGGCTTCCGTATGC<br>TCAGGCGGCGGAAAGCGTGATTGAC<br>GTATCGCCAGCTTTTGCAAACGCCC<br>ATTTAAGTGAGAAAACCGGCAGCCA<br>GTGGTCAGCGAGCCCACGGGTCATCA<br>GAACGCTATCAGGGGCAAGTTTGCA<br>GATCGATCCAGGCCTAATCGATCGG<br>TGGGGCGGACAAGGCACTCGCGCCG | A (3 and 4)<br>G (2, 3, and 4)<br>C (2, 2, and 3)<br>T (3 and 4) | SEQ ID NO: 109 |
| ATGACGCCAGAGGGCTGGAGATGCA<br>TACTGGCAAATAAAGTACGTTCCAC<br>CTCGCGGTAAATTTACCGAAGCACA<br>GTGTTTATCATCCCTATTGCTTTGC<br>GTTCGTCCGTGAAAATAAGAGTCAC<br>GTCACCTGCTGCCCCACGTGGGACA<br>TCTTGCACAAAGGGGAGAAGCAATT<br>TGTTGAACTACTTTTCCTGATATGT<br>TACGACTGCGAAGGCTTCTTCGTTG<br>ACGCTTATCAGGCCTACGCCATCTC | A (3 and 4)<br>G (2, 3, and 4)<br>C (2, 3, and 4)<br>T (3 and 4) | SEQ ID NO: 110 |
| GTCCGGCACTGAAAATCGTTGATGC<br>CTTTGACACCATTTTCCGTAGTGAA<br>TTGCGGCGGTAGCCAGCTGGAAGGA<br>CAACGGGTTATAGGCACCGCCAGGG<br>TATCCAAATTTTTGGCCGTTCACTG<br>GTTTGCCGAGGCAATATATGTCCGG<br>TCTGGCGGCAATTTTGCTGATGGAT<br>TCAACGTGAAGCCCTGTTTAACGCT<br>CACCAGAATCAGGGCAAACATATTC<br>CTGCTGCCAGATTTTCACCTGCTGA | A (2 and 4)<br>G (2, 2, and 3)<br>C (2 and 3)<br>T (4, 4, and 4) | SEQ ID NO: 111 |
| TATGGAAGCGGCCCAGATAAGCCAG<br>CCTGGTCTGGAGGGCAATACGCCCT<br>CTGACGCTGCCAAACGCCGACCGCG<br>TGGCGGCGAAATTTCGCGCCAGCGG<br>TTTGCTGGAAAAATTGCGCGCCAAA<br>CGATCGTCGCGGCCTGAATACCTGG<br>CTTCCTCGATTGGGGCTGGCGTATT<br>ATGCGCGCGTTAAAGTGCGTATCAC<br>TCAATGGTGACTTTTGCCGTTCCCG<br>GGAATCGCCCTGGGGCGGCGCACAA | A (3 and 3)<br>G (3, 4, and 4)<br>C (2 and 3)<br>T (2, 3, and 4) | SEQ ID NO: 112 |

What is claimed:

1. A test or control nucleic acid comprising a test or control sequence, the test or control sequence comprising:
   an artificial sequence combined from a plurality of extracted sequences, wherein each extracted sequence is extracted from a context sequence comprising a respective locus of a representative set of error prone loci, the loci comprising:
   an approximately equal number of loci involving errors in A, T, C, and G homopolymers;
   an approximately equal number of loci involving homopolymers having a length of two, three, and four; or
   both the approximately equal number of loci involving errors in A, T, C, and G homopolymers, and the approximately equal number of loci involving homopolymers having a length of two, three, and four; and
   wherein the plurality of extracted sequences comprise at least one sequence extracted from SEQ ID NOS 1-102.

2. The test or control nucleic acid of claim 1, wherein the test or control sequence comprises a sequence further including one or more sequencing adapters to the combined sequence.

3. The test or control nucleic acid of claim 1, wherein the test or control sequence comprises a sequence further determined by finding co-occurring variant locations present in at least three and no more than twenty sequencing runs included in a training set of sequencing runs.

4. The test or control nucleic acid of claim 1, wherein the test or control sequence comprises a sequence further determined by finding co-occurring variant locations present in at least five and no more than fifteen sequencing runs included in a training set of sequencing runs.

5. The test or control nucleic acid of claim 1, wherein the representative set of error prone loci comprises both the approximately equal number of loci involving errors in A, T, C, and G homopolymers, and the approximately equal number of loci involving homopolymers having a length of two, three, and four.

6. The test or control nucleic acid of claim 1, wherein the approximately equal number of A, T, C, and G homopolymers, lengths, or both equals at least two.

7. The test or control nucleic acid of claim 1, wherein the approximately equal number of A, T, C, and G homopolymers, lengths, or both equals at least three.

8. The test or control nucleic acid of claim 1, wherein the approximately equal number of A, T, C, and G homopolymers, lengths, or both equals at least four.

9. The test or control nucleic acid of claim 1, where the representative set of error prone loci comprises all four A, T, C, and G homopolymers.

10. The test or control nucleic acid of claim 9, where the representative set of error prone loci comprises three homopolymer loci for each of two A, T, C or G nucleotides and two homopolymer loci for each of the two alternative A, T, C, or G nucleotides.

11. The test or control nucleic acid of claim 9, wherein the lengths are selected from two, three, four, or a combination thereof.

12. The test or control nucleic acid of claim 1, wherein the test or control sequence is attached to a solid phase support.

13. The test or control nucleic acid of claim 12, wherein the solid phase support is disposed on a sensor array.

14. The test or control nucleic acid of claim 1, wherein the artificial sequence is at least one of SEQ ID NOS 103-112.

* * * * *

SEQUENCE LISTING

<160> NUMBER OF SEQ ID NOS: 114

<210> SEQ ID NO 1
<211> LENGTH: 25
<212> TYPE: DNA
<213> ORGANISM: Escherichia coli DH10B

<400> SEQUENCE: 1
gatgcagcac cgaaggctga atatc                           25

<210> SEQ ID NO 2
<211> LENGTH: 25
<212> TYPE: DNA
<213> ORGANISM: Escherichia coli DH10B

```
<400> SEQUENCE: 2
tctcaggtta cgaaggcggt gccaa                                           25

<210> SEQ ID NO 3
<211> LENGTH: 25
<212> TYPE: DNA
<213> ORGANISM: Escherichia coli DH10B

<400> SEQUENCE: 3
ttgatcgact ttaacgtccg tgcgg                                           25

<210> SEQ ID NO 4
<211> LENGTH: 25
<212> TYPE: DNA
<213> ORGANISM: Escherichia coli DH10B

<400> SEQUENCE: 4
agccccggct gtaacgtttt ggtat                                           25

<210> SEQ ID NO 5
<211> LENGTH: 25
<212> TYPE: DNA
<213> ORGANISM: Escherichia coli DH10B

<400> SEQUENCE: 5
gtttgccgag gcaatatatg tccgg                                           25

<210> SEQ ID NO 6
<211> LENGTH: 25
<212> TYPE: DNA
<213> ORGANISM: Escherichia coli DH10B

<400> SEQUENCE: 6
ccgccgaagg ccaaccccag tttga                                           25

<210> SEQ ID NO 7
<211> LENGTH: 25
<212> TYPE: DNA
<213> ORGANISM: Escherichia coli DH10B

<400> SEQUENCE: 7
acagcggcgg gaaatttccc acctg                                           25

<210> SEQ ID NO 8
<211> LENGTH: 25
<212> TYPE: DNA
<213> ORGANISM: Escherichia coli DH10B

<400> SEQUENCE: 8
gtgggtcagc gaaacgtttc gctga                                           25

<210> SEQ ID NO 9
<211> LENGTH: 25
<212> TYPE: DNA
<213> ORGANISM: Escherichia coli DH10B

<400> SEQUENCE: 9
agcggaacag taaatttacg gcaga                                           25

<210> SEQ ID NO 10
<211> LENGTH: 25
<212> TYPE: DNA
<213> ORGANISM: Escherichia coli DH10B
```

```
<400> SEQUENCE: 10
gttatgaacc caaagtcagc cgtga                                     25

<210> SEQ ID NO 11
<211> LENGTH: 25
<212> TYPE: DNA
<213> ORGANISM: Escherichia coli DH10B

<400> SEQUENCE: 11 gactgcccctt taaacctgta cccac                                    25

<210> SEQ ID NO 12
<211> LENGTH: 25
<212> TYPE: DNA
<213> ORGANISM: Escherichia coli DH10B

<400> SEQUENCE: 12
tactggcaaa taaagtacgt tccac                                     25

<210> SEQ ID NO 13
<211> LENGTH: 25
<212> TYPE: DNA
<213> ORGANISM: Escherichia coli DH10B

<400> SEQUENCE: 13
aagagcgtcg taaagtattg caggt                                     25

<210> SEQ ID NO 14
<211> LENGTH: 25
<212> TYPE: DNA
<213> ORGANISM: Escherichia coli DH10B

<400> SEQUENCE: 14
tcaggcggcg gaaagcgtga ttgac                                     25

<210> SEQ ID NO 15
<211> LENGTH: 25
<212> TYPE: DNA
<213> ORGANISM: Escherichia coli DH10B

<400> SEQUENCE: 15
ctgacgctgc caaacgccga ccgcg                                     25

<210> SEQ ID NO 16
<211> LENGTH: 25
<212> TYPE: DNA
<213> ORGANISM: Escherichia coli DH10B

<400> SEQUENCE: 16
atgcgcgcgt taaagtgcgt atcac                                     25

<210> SEQ ID NO 17
<211> LENGTH: 25
<212> TYPE: DNA
<213> ORGANISM: Escherichia coli DH10B

<400> SEQUENCE: 17
atggttactt taaaaccgga ttaat                                     25

<210> SEQ ID NO 18
<211> LENGTH: 25
<212> TYPE: DNA
```

<213> ORGANISM: Escherichia coli DH10B

<400> SEQUENCE: 18
catcaggcac caaaagagta tggcg                                    25

<210> SEQ ID NO 19
<211> LENGTH: 25
<212> TYPE: DNA
<213> ORGANISM: Escherichia coli DH10B

<400> SEQUENCE: 19
acttcggcac caaaagcatt ggcgt                                    25

<210> SEQ ID NO 20
<211> LENGTH: 25
<212> TYPE: DNA
<213> ORGANISM: Escherichia coli DH10B

<400> SEQUENCE: 20
gcgggaaggg gaaaatccat gctga                                    25

<210> SEQ ID NO 21
<211> LENGTH: 25
<212> TYPE: DNA
<213> ORGANISM: Escherichia coli DH10B

<400> SEQUENCE: 21
gttcgtccgt gaaaataaga gtcac                                    25

<210> SEQ ID NO 22
<211> LENGTH: 25
<212> TYPE: DNA
<213> ORGANISM: Escherichia coli DH10B

<400> SEQUENCE: 22
atttaagtga gaaaaccggc agcca                                    25

<210> SEQ ID NO 23
<211> LENGTH: 25
<212> TYPE: DNA
<213> ORGANISM: Escherichia coli DH10B

<400> SEQUENCE: 23
cgaaatttga taaaatcccg ctctt                                    25

<210> SEQ ID NO 24
<211> LENGTH: 25
<212> TYPE: DNA
<213> ORGANISM: Escherichia coli DH10B

<400> SEQUENCE: 24
gcttgatcag gaaaagtttg gtatc                                    25

<210> SEQ ID NO 25
<211> LENGTH: 25
<212> TYPE: DNA
<213> ORGANISM: Escherichia coli DH10B

<400> SEQUENCE: 25
gtccggcact gaaaatcgtt gatgc                                    25

<210> SEQ ID NO 26
<211> LENGTH: 25

```
<212> TYPE: DNA
<213> ORGANISM: Escherichia coli DH10B

<400> SEQUENCE: 26
gctggcggag ccttcagtct atttt                                 25

<210> SEQ ID NO 27
<211> LENGTH: 25
<212> TYPE: DNA
<213> ORGANISM: Escherichia coli DH10B

<400> SEQUENCE: 27
ctggaacgcc ccttcaacct tagca                                 25

<210> SEQ ID NO 28
<211> LENGTH: 25
<212> TYPE: DNA
<213> ORGANISM: Escherichia coli DH10B

<400> SEQUENCE: 28
aaggcgcagg gtttgcagag ctgtt                                 25

<210> SEQ ID NO 29
<211> LENGTH: 25
<212> TYPE: DNA
<213> ORGANISM: Escherichia coli DH10B

<400> SEQUENCE: 29
gccaccagcc ctttgctttc cagtg                                 25

<210> SEQ ID NO 30
<211> LENGTH: 25
<212> TYPE: DNA
<213> ORGANISM: Escherichia coli DH10B

<400> SEQUENCE: 30
gtaccggcaa atttgccgcc gtaag                                 25

<210> SEQ ID NO 31
<211> LENGTH: 25
<212> TYPE: DNA
<213> ORGANISM: Escherichia coli DH10B

<400> SEQUENCE: 31
gtcggcgcaa atttgcaacc agaag                                 25

<210> SEQ ID NO 32
<211> LENGTH: 25
<212> TYPE: DNA
<213> ORGANISM: Escherichia coli DH10B

<400> SEQUENCE: 32
gcgtgaccaa atttggtgca gcgcc                                 25

<210> SEQ ID NO 33
<211> LENGTH: 25
<212> TYPE: DNA
<213> ORGANISM: Escherichia coli DH10B

<400> SEQUENCE: 33
gcggcgggaa atttcccacc tgata                                 25

<210> SEQ ID NO 34
```

```
<211> LENGTH: 25
<212> TYPE: DNA
<213> ORGANISM: Escherichia coli DH10B

<400> SEQUENCE: 34
ctcgcggtaa atttaccgaa gcaca                                          25

<210> SEQ ID NO 35
<211> LENGTH: 25
<212> TYPE: DNA
<213> ORGANISM: Escherichia coli DH10B

<400> SEQUENCE: 35
tcccaaaccg gtttcgttta ataat                                          25

<210> SEQ ID NO 36
<211> LENGTH: 25
<212> TYPE: DNA
<213> ORGANISM: Escherichia coli DH10B

<400> SEQUENCE: 36
tggcggcgaa atttcgcgcc agcgg                                          25

<210> SEQ ID NO 37
<211> LENGTH: 25
<212> TYPE: DNA
<213> ORGANISM: Escherichia coli DH10B

<400> SEQUENCE: 37
tccgttacac cttttccaca ttcac                                          25

<210> SEQ ID NO 38
<211> LENGTH: 25
<212> TYPE: DNA
<213> ORGANISM: Escherichia coli DH10B

<400> SEQUENCE: 38
tgtgtcaggg cttttggttc tccct                                          25

<210> SEQ ID NO 39
<211> LENGTH: 25
<212> TYPE: DNA
<213> ORGANISM: Escherichia coli DH10B

<400> SEQUENCE: 39
tctgcaattc attttgcata tagcc                                          25

<210> SEQ ID NO 40
<211> LENGTH: 25
<212> TYPE: DNA
<213> ORGANISM: Escherichia coli DH10B

<400> SEQUENCE: 40
cataactatt gttttgatga atcag                                          25

<210> SEQ ID NO 41
<211> LENGTH: 25
<212> TYPE: DNA
<213> ORGANISM: Escherichia coli DH10B

<400> SEQUENCE: 41
gtatcgccag cttttgcaaa cgccc                                          25
```

```
<210> SEQ ID NO 42
<211> LENGTH: 25
<212> TYPE: DNA
<213> ORGANISM: Escherichia coli DH10B

<400> SEQUENCE: 42
acgctgcatc gttttcatct ttaaa                                    25

<210> SEQ ID NO 43
<211> LENGTH: 25
<212> TYPE: DNA
<213> ORGANISM: Escherichia coli DH10B

<400> SEQUENCE: 43
agatagctcc cttttggcat gaaga                                    25

<210> SEQ ID NO 44
<211> LENGTH: 25
<212> TYPE: DNA
<213> ORGANISM: Escherichia coli DH10B

<400> SEQUENCE: 44
tgttgaacta cttttcctga tatgt                                    25

<210> SEQ ID NO 45
<211> LENGTH: 25
<212> TYPE: DNA
<213> ORGANISM: Escherichia coli DH10B

<400> SEQUENCE: 45
aaccagcact cttttcatgg ctatc                                    25

<210> SEQ ID NO 46
<211> LENGTH: 25
<212> TYPE: DNA
<213> ORGANISM: Escherichia coli DH10B

<400> SEQUENCE: 46
acaggacgcc attttgccga ctccc                                    25

<210> SEQ ID NO 47
<211> LENGTH: 25
<212> TYPE: DNA
<213> ORGANISM: Escherichia coli DH10B

<400> SEQUENCE: 47
tctggcggca attttgctga tggat                                    25

<210> SEQ ID NO 48
<211> LENGTH: 25
<212> TYPE: DNA
<213> ORGANISM: Escherichia coli DH10B

<400> SEQUENCE: 48
tcaatggtga cttttgccgt tcccg                                    25

<210> SEQ ID NO 49
<211> LENGTH: 25
<212> TYPE: DNA
<213> ORGANISM: Escherichia coli DH10B

<400> SEQUENCE: 49
ctgctgccag attttcacct gctga                                    25
```

```
<210> SEQ ID NO 50
<211> LENGTH: 25
<212> TYPE: DNA
<213> ORGANISM: Escherichia coli DH10B

<400> SEQUENCE: 50
ctttgacacc attttccgta gtgaa                                              25

<210> SEQ ID NO 51
<211> LENGTH: 25
<212> TYPE: DNA
<213> ORGANISM: Escherichia coli DH10B

<400> SEQUENCE: 51
gttcgagtcc ggccttcggc accaa                                              25

<210> SEQ ID NO 52
<211> LENGTH: 25
<212> TYPE: DNA
<213> ORGANISM: Escherichia coli DH10B

<400> SEQUENCE: 52
agggatggga cgcctgtttg ccatc                                              25

<210> SEQ ID NO 53
<211> LENGTH: 25
<212> TYPE: DNA
<213> ORGANISM: Escherichia coli DH10B

<400> SEQUENCE: 53
gatcgatcca ggcctaatcg atcgg                                              25

<210> SEQ ID NO 54
<211> LENGTH: 25
<212> TYPE: DNA
<213> ORGANISM: Escherichia coli DH10B

<400> SEQUENCE: 54
acgcttatca ggcctacgcc atctc                                              25

<210> SEQ ID NO 55
<211> LENGTH: 25
<212> TYPE: DNA
<213> ORGANISM: Escherichia coli DH10B

<400> SEQUENCE: 55
gtggtcagcg agccacgggt catca                                              25

<210> SEQ ID NO 56
<211> LENGTH: 25
<212> TYPE: DNA
<213> ORGANISM: Escherichia coli DH10B

<400> SEQUENCE: 56
agcaggtgac ggccttcatg atcgg                                              25

<210> SEQ ID NO 57
<211> LENGTH: 25
<212> TYPE: DNA
<213> ORGANISM: Escherichia coli DH10B

<400> SEQUENCE: 57
ttgcggcggt agccagctgg aagga                                              25
```

<210> SEQ ID NO 58
<211> LENGTH: 25
<212> TYPE: DNA
<213> ORGANISM: Escherichia coli DH10B

<400> SEQUENCE: 58
cgatcgtcgc ggcctgaata cctgg                                     25

<210> SEQ ID NO 59
<211> LENGTH: 25
<212> TYPE: DNA
<213> ORGANISM: Escherichia coli DH10B

<400> SEQUENCE: 59
ggaaagcgat ggcctacggc gagcg                                     25

<210> SEQ ID NO 60
<211> LENGTH: 25
<212> TYPE: DNA
<213> ORGANISM: Escherichia coli DH10B

<400> SEQUENCE: 60
tacctgcgcc gccctggtag acgtc                                     25

<210> SEQ ID NO 61
<211> LENGTH: 25
<212> TYPE: DNA
<213> ORGANISM: Escherichia coli DH10B

<400> SEQUENCE: 61
aggcgacaat gccctggtct ttcgc                                     25

<210> SEQ ID NO 62
<211> LENGTH: 25
<212> TYPE: DNA
<213> ORGANISM: Escherichia coli DH10B

<400> SEQUENCE: 62
gggctaagtg gccctggtgg actcg                                     25

<210> SEQ ID NO 63
<211> LENGTH: 25
<212> TYPE: DNA
<213> ORGANISM: Escherichia coli DH10B

<400> SEQUENCE: 63
aggcaatcga gcccagatgc cggat                                     25

<210> SEQ ID NO 64
<211> LENGTH: 25
<212> TYPE: DNA
<213> ORGANISM: Escherichia coli DH10B

<400> SEQUENCE: 64
cgttgattct gcccttattt acaaa                                     25

<210> SEQ ID NO 65
<211> LENGTH: 25
<212> TYPE: DNA
<213> ORGANISM: Escherichia coli DH10B

<400> SEQUENCE: 65
gaataatcca gcccgccagg catgg    25

<210> SEQ ID NO 66
<211> LENGTH: 25
<212> TYPE: DNA
<213> ORGANISM: Escherichia coli DH10B

<400> SEQUENCE: 66
caggcaagcc gcccaggtgc tcaca    25

<210> SEQ ID NO 67
<211> LENGTH: 25
<212> TYPE: DNA
<213> ORGANISM: Escherichia coli DH10B

<400> SEQUENCE: 67
gtgtttatca tccctattgc tttgc    25

<210> SEQ ID NO 68
<211> LENGTH: 25
<212> TYPE: DNA
<213> ORGANISM: Escherichia coli DH10B

<400> SEQUENCE: 68
tatggaagcg gcccagataa gccag    25

<210> SEQ ID NO 69
<211> LENGTH: 25
<212> TYPE: DNA
<213> ORGANISM: Escherichia coli DH10B

<400> SEQUENCE: 69
tcaacgtgaa gccctgttta acgct    25

<210> SEQ ID NO 70
<211> LENGTH: 25
<212> TYPE: DNA
<213> ORGANISM: Escherichia coli DH10B

<400> SEQUENCE: 70
tgatattcct gcccctgata gcggt    25

<210> SEQ ID NO 71
<211> LENGTH: 25
<212> TYPE: DNA
<213> ORGANISM: Escherichia coli DH10B

<400> SEQUENCE: 71
atgccgccag tcccctgatg acccg    25

<210> SEQ ID NO 72
<211> LENGTH: 25
<212> TYPE: DNA
<213> ORGANISM: Escherichia coli DH10B

<400> SEQUENCE: 72
cggtcgtgcg accccggtag agctg    25

<210> SEQ ID NO 73
<211> LENGTH: 25
<212> TYPE: DNA
<213> ORGANISM: Escherichia coli DH10B

<400> SEQUENCE: 73
tgttatatct gccccgataa aacgg        25

<210> SEQ ID NO 74
<211> LENGTH: 25
<212> TYPE: DNA
<213> ORGANISM: Escherichia coli DH10B

<400> SEQUENCE: 74
aagccaatca gccctatca accgc         25

<210> SEQ ID NO 75
<211> LENGTH: 25
<212> TYPE: DNA
<213> ORGANISM: Escherichia coli DH10B

<400> SEQUENCE: 75
gtcacctgct gccccacgtg ggaca        25

<210> SEQ ID NO 76
<211> LENGTH: 25
<212> TYPE: DNA
<213> ORGANISM: Escherichia coli DH10B

<400> SEQUENCE: 76
cacaggtgat atggccttcg ccaga        25

<210> SEQ ID NO 77
<211> LENGTH: 25
<212> TYPE: DNA
<213> ORGANISM: Escherichia coli DH10B

<400> SEQUENCE: 77
agctacccga taggcttccg ccatc        25

<210> SEQ ID NO 78
<211> LENGTH: 25
<212> TYPE: DNA
<213> ORGANISM: Escherichia coli DH10B

<400> SEQUENCE: 78
tacgactgcg aaggcttctt cgttg        25

<210> SEQ ID NO 79
<211> LENGTH: 25
<212> TYPE: DNA
<213> ORGANISM: Escherichia coli DH10B

<400> SEQUENCE: 79
tggggcggac aaggcactcg cgccg        25

<210> SEQ ID NO 80
<211> LENGTH: 25
<212> TYPE: DNA
<213> ORGANISM: Escherichia coli DH10B

<400> SEQUENCE: 80
caacgggtta taggcaccgc caggg        25

<210> SEQ ID NO 81
<211> LENGTH: 25
<212> TYPE: DNA
<213> ORGANISM: Escherichia coli DH10B

<400> SEQUENCE: 81
tagcggtaaa cgggctaccg gtatc                                          25

<210> SEQ ID NO 82
<211> LENGTH: 25
<212> TYPE: DNA
<213> ORGANISM: Escherichia coli DH10B

<400> SEQUENCE: 82
tgattgcaac agggcaaatt gcgca                                          25

<210> SEQ ID NO 83
<211> LENGTH: 25
<212> TYPE: DNA
<213> ORGANISM: Escherichia coli DH10B

<400> SEQUENCE: 83
tgcatgaggt cgggttgaat atcaa                                          25

<210> SEQ ID NO 84
<211> LENGTH: 25
<212> TYPE: DNA
<213> ORGANISM: Escherichia coli DH10B

<400> SEQUENCE: 84
tttctgttcc agggcttccg ccacc                                          25

<210> SEQ ID NO 85
<211> LENGTH: 25
<212> TYPE: DNA
<213> ORGANISM: Escherichia coli DH10B

<400> SEQUENCE: 85
atgacgccag agggctggag atgca                                          25

<210> SEQ ID NO 86
<211> LENGTH: 25
<212> TYPE: DNA
<213> ORGANISM: Escherichia coli DH10B

<400> SEQUENCE: 86
tcgatccttg agggatgatt gcatt                                          25

<210> SEQ ID NO 87
<211> LENGTH: 25
<212> TYPE: DNA
<213> ORGANISM: Escherichia coli DH10B

<400> SEQUENCE: 87
tgcggcatac tgggcttccg tatgc                                          25

<210> SEQ ID NO 88
<211> LENGTH: 25
<212> TYPE: DNA
<213> ORGANISM: Escherichia coli DH10B

<400> SEQUENCE: 88
tgatatcatc agggcagacc ggtta                                          25

<210> SEQ ID NO 89
<211> LENGTH: 25
<212> TYPE: DNA
<213> ORGANISM: Escherichia coli DH10B

<400> SEQUENCE: 89
caccagaatc agggcaaaca tattc                                         25

<210> SEQ ID NO 90
<211> LENGTH: 25
<212> TYPE: DNA
<213> ORGANISM: Escherichia coli DH10B

<400> SEQUENCE: 90
cctggtctgg aggcaatac gccct                                          25

<210> SEQ ID NO 91
<211> LENGTH: 25
<212> TYPE: DNA
<213> ORGANISM: Escherichia coli DH10B

<400> SEQUENCE: 91
atcaccgaat cggggaccac cgcca                                         25

<210> SEQ ID NO 92
<211> LENGTH: 25
<212> TYPE: DNA
<213> ORGANISM: Escherichia coli DH10B

<400> SEQUENCE: 92
gcccataaat tgggctgat ctcca                                          25

<210> SEQ ID NO 93
<211> LENGTH: 25
<212> TYPE: DNA
<213> ORGANISM: Escherichia coli DH10B

<400> SEQUENCE: 93
acaggctaag aggggccgga caccc                                         25

<210> SEQ ID NO 94
<211> LENGTH: 25
<212> TYPE: DNA
<213> ORGANISM: Escherichia coli DH10B

<400> SEQUENCE: 94
ccctgaaggc cggggcagcc cacat                                         25

<210> SEQ ID NO 95
<211> LENGTH: 25
<212> TYPE: DNA
<213> ORGANISM: Escherichia coli DH10B

<400> SEQUENCE: 95
gattcggcaa agggagata cggtt                                          25

<210> SEQ ID NO 96
<211> LENGTH: 25
<212> TYPE: DNA
<213> ORGANISM: Escherichia coli DH10B

<400> SEQUENCE: 96
tatagaggat cggggccacg cgcgc                                         25

<210> SEQ ID NO 97
<211> LENGTH: 25
<212> TYPE: DNA

<213> ORGANISM: Escherichia coli DH10B

<400> SEQUENCE: 97
tcttgcacaa aggggagaag caatt　　　　　　　　　　　　　　　　　　　25

<210> SEQ ID NO 98
<211> LENGTH: 25
<212> TYPE: DNA
<213> ORGANISM: Escherichia coli DH10B

<400> SEQUENCE: 98
gaacgctatc agggggcaagt ttgca　　　　　　　　　　　　　　　　　　　25

<210> SEQ ID NO 99
<211> LENGTH: 25
<212> TYPE: DNA
<213> ORGANISM: Escherichia coli DH10B

<400> SEQUENCE: 99
cttcctcgat tggggctggc gtatt　　　　　　　　　　　　　　　　　　　25

<210> SEQ ID NO 100
<211> LENGTH: 25
<212> TYPE: DNA
<213> ORGANISM: Escherichia coli DH10B

<400> SEQUENCE: 100
ggaatcgccc tggggcggcg cacaa　　　　　　　　　　　　　　　　　　　25

<210> SEQ ID NO 101
<211> LENGTH: 25
<212> TYPE: DNA
<213> ORGANISM: Escherichia coli DH10B

<400> SEQUENCE: 101
tatccaaatt tttggccgtt cactg　　　　　　　　　　　　　　　　　　　25

<210> SEQ ID NO 102
<211> LENGTH: 25
<212> TYPE: DNA
<213> ORGANISM: Escherichia coli DH10B

<400> SEQUENCE: 102
tttgctggaa aaattgcgcg ccaaa　　　　　　　　　　　　　　　　　　　25

<210> SEQ ID NO 103
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 103
gatgcagcac cgaaggctga atatctagcg gtaaacgggc taccggtatc tgatattcct　　60 gccctgata gcggtgccac cagcccttg ctttccagtg catcaggcac caaaagagta　120 tggcgtacct gcgccgccct ggtagacgtc acaggctaag aggggccgga cacccgttat　180 gaacccaaag tcagccgtga cataactatt gttttgatga atcagagcta cccgataggc　240 ttccgccatc　　　　　　　　　　　　　　　　　　　　　　　　　　　　　　250

<210> SEQ ID NO 104

```
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 104
gctggcggag ccttcagtct attttgggct aagtggccct ggtggactcg atggttactt     60
taaaaccgga ttaattgatt gcaacagggc aaattgcgca tgtgtcaggg cttttggttc    120
tccctagcgg aacagtaaat ttacggcaga cggtcgtgcg accccggtag agctggtcgg    180
cgcaaatttg caaccagaag ccctgaaggc cggggcagcc cacataggga tgggacgcct    240
gtttgccatc                                                           250

<210> SEQ ID NO 105
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 105
gttcgagtcc ggccttcggc accaaaaggc gcagggtttg cagagctgtt atcaccgaat     60
cggggaccac cgccagtggg tcagcgaaac gtttcgctga atgccgccag tcccctgatg    120
acccgtgcat gaggtcgggt tgaatatcaa tctgcaattc attttgcata tagccaggca    180
atcgagccca gatgccggat gcgggaaggg gaaaatccat gctgactgga acgccccttc    240
aaccttagca                                                           250

<210> SEQ ID NO 106
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 106
cacaggtgat atggccttcg ccagaacagc ggcgggaaat ttcccacctg tccgttacac     60
cttttccaca ttcacaggcg acaatgccct ggtctttcgc gcccataaat tggggctgat    120
ctccagtacc ggcaaatttg ccgccgtaag acttcggcac caaaagcatt ggcgttttct    180
gttccagggc ttccgccacc tgttatatct gccccgataa aacggtctca ggttacgaag    240
gcggtgccaa                                                           250

<210> SEQ ID NO 107
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 107
gactgccctt taaacctgta cccactcgat ccttgaggga tgattgcatt caggcaagcc     60
gcccaggtgc tcacatccca aaccggtttc gtttaataat gattcggcaa aggggagata    120
cggttacgct gcatcgtttt catctttaaa cgaaatttga taaatcccg ctcttagcag     180 gtgacggcct tcatgatcgg ttgatcgact ttaacgtccg tgcggacagg acgccatttt    240
```

```
gccgactccc                                                           250

<210> SEQ ID NO 108
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 108
gcgtgaccaa atttggtgca gcgccgaata atccagcccg ccaggcatgg aagagcgtcg     60
taaagtattg caggttgata tcatcagggc agaccggtta aagccaatca gcccctatca   120
accgctatag aggatcgggg ccacgcgcgc agatagctcc cttttggcat gaagagcttg   180
atcaggaaaa gtttggtatc aaccagcact cttttcatgg ctatcagccc cggctgtaac   240
gttttggtat                                                           250

<210> SEQ ID NO 109
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 109
cgttgattct gcccttattt acaaagcggc gggaaatttc ccacctgata tgcggcatac     60
tgggcttccg tatgctcagg cggcggaaag cgtgattgac gtatcgccag cttttgcaaa   120
cgcccattta agtgagaaaa ccggcagcca gtggtcagcg agccacgggt catcagaacg   180
ctatcagggg caagtttgca gatcgatcca ggcctaatcg atcggtgggg cggacaaggc   240
actcgcgccg                                                           250

<210> SEQ ID NO 110
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 110
atgacgccag agggctggag atgcatactg gcaaataaag tacgttccac ctcgcggtaa     60
atttaccgaa gcacagtgtt tatcatccct attgctttgc gttcgtccgt gaaaataaga   120
gtcacgtcac ctgctgcccc acgtgggaca tcttgcacaa aggggagaag caatttgttg   180
aactactttt cctgatatgt tacgactgcg aaggcttctt cgttgacgct tatcaggcct   240
acgccatctc                                                           250

<210> SEQ ID NO 111
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 111
gtccggcact gaaaatcgtt gatgcctttg acaccatttt ccgtagtgaa ttgcggcggt     60
```

```
agccagctgg aaggacaacg ggttataggc accgccaggg tatccaaatt tttggccgtt    120
cactggtttg ccgaggcaat atatgtccgg tctggcggca attttgctga tggattcaac    180
gtgaagccct gtttaacgct caccagaatc agggcaaaca tattcctgct gccagatttt    240
cacctgctga                                                           250
```

<210> SEQ ID NO 112
<211> LENGTH: 250
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 112

```
tatggaagcg gcccagataa gccagcctgg tctggagggc aatacgccct ctgacgctgc     60
caaacgccga ccgcgtggcg gcgaaatttc gcgccagcgg tttgctggaa aaattgcgcg    120
ccaaacgatc gtcgcggcct gaatacctgg cttcctcgat tggggctggc gtattatgcg    180
cgcgttaaag tgcgtatcac tcaatggtga cttttgccgt tcccgggaat cgccctgggg    240
cggcgcacaa                                                           250
```

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 113

```
ccatctcatc cctgcgtgtc tccgacatcg                                      30
```

<210> SEQ ID NO 114
<211> LENGTH: 41
<212> TYPE: DNA
<213> ORGANISM: Artificial Sequence
<220> FEATURE:
<223> OTHER INFORMATION: Description of Artificial Sequence: Synthetic
      Polynucleotide

<400> SEQUENCE: 114

```
atcaccgact gcccatagag aggaaagcgg aggcgtagtg g                         41
```